(12) United States Patent
Iwakura et al.

(10) Patent No.: US 9,175,054 B2
(45) Date of Patent: Nov. 3, 2015

(54) CTRP6 WHICH CAN BE USED AS THERAPEUTIC AND PROPHYLACTIC AGENT FOR AUTOIMMUNE DISEASES

(75) Inventors: Yoichiro Iwakura, Tokyo (JP); Masanori Murayama, Tokyo (JP); Harumichi Ishigame, Tokyo (JP); Shigeru Kakuta, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 14/116,039

(22) PCT Filed: May 9, 2012

(86) PCT No.: PCT/JP2012/061827
§ 371 (c)(1),
(2), (4) Date: Feb. 12, 2014

(87) PCT Pub. No.: WO2012/157479
PCT Pub. Date: Nov. 22, 2012

(65) Prior Publication Data
US 2014/0194343 A1 Jul. 10, 2014

Related U.S. Application Data

(60) Provisional application No. 61/485,746, filed on May 13, 2011.

(30) Foreign Application Priority Data

Oct. 3, 2011 (JP) ................................. 2011-219350

(51) Int. Cl.
| | | |
|---|---|---|
| A61K 38/00 | (2006.01) | |
| C07K 14/47 | (2006.01) | |
| A61P 37/02 | (2006.01) | |
| A61K 38/17 | (2006.01) | |
| C07K 14/575 | (2006.01) | |

(52) U.S. Cl.
CPC .............. *C07K 14/47* (2013.01); *A61K 38/1709* (2013.01); *C07K 14/5759* (2013.01)

(58) Field of Classification Search
CPC . A61K 38/1709; C07K 14/47; C07K 14/5759
See application file for complete search history.

(56) References Cited

U.S. PATENT DOCUMENTS

| 2004/0248156 A1 | 12/2004 | Hu et al. |
| 2005/0266464 A1 | 12/2005 | Marshall et al. |

FOREIGN PATENT DOCUMENTS

| WO | WO 00/73446 A2 * | 12/2000 | ............. C12N 15/12 |
| WO | 2005/087255 | 9/2005 | |
| WO | 2005087254 A2 | 9/2005 | |

OTHER PUBLICATIONS

Rudinger, Peptide Hormones, JA Parsons, Ed., 1976, pp. 1-7.*
SIGMA, 2004, pp. 1-2.*
Berendsen, A Glimpse of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
List of Autoimmune and Autoimmune-Related Diseases, from http://www.aarda.org/autoimmune-information/list-of-diseases/, pp. 1-5, accessed Dec. 5, 2014.*
Understanding autoimmune diseases, from NIH, pp. 1-3, published on Oct. 2012.*
Familian et al, Infliximab treatment reduces complement activation in patients with rheumatoid arthritis, Ann Rheum Dis, 2005, 64, pp. 1003-1008.*
International Search Report, dated Jun. 12, 2012, which issued during the prosecution of International Patent Application PCT/JP2012/061827, which corresponds to the present application.
Written Opinion, dated Jun. 12, 2012, which issued during the prosecution of International Patent Application PCT/JP2012/061827, which corresponds to the present application.
Uday Kishore, et al., "C1q and tumor necrosis factor superfamily: modularity and versatility," Trends in Immunology, October, pp. 551-561 vol. 25 No. 10, Elsevier, Oxford, UK, 2004.
Min-Jin Kim, et al., "C1qTNF-Related Protein-6 Increases the Expression of Interleukin-10 in Macrophages", Molecules and Cells, 2010, pp. 59-64, vol. 30, No. 1, Springer, Kyungju, Korea.
E. Keystone, et al., "IL-10 as a therapeutic strategy in the treatment of rheumatoid arthritis," Rheumatic Disease Clinics of North America, 1998, pp. 629-639, vol. 24, No. 3, Toronto, Canada.
Guang W. Wong, et al., "A family of Acrp30/adiponectin structural and functional paralogs", PNAS, 2004, pp. 10302-10307 vol. 101, No. 28, The National Academy of Sciences of the USA, Cambridge, MA.
Stephen Eyre, et al., "Overlapping genetic susceptibility variants between three autoimmune disorders rheumatoid arthritis, type 1 diabetes and coeliac disease", Arthritis Research & Therapy, 2010, p. R175, vol. 12, No. 5, BioMed Central, Manchester, UK.
Ying Jin, et al., "Variant of TYR and autoimmunity susceptibility Loci in generalized vitiligo," New England Journal of Medicine, 2010, pp. 1686-1697, vol. 362, No. 18, Massachusetts Medical Society.
Yoichiro Iwakura, "Kansetsuen Hassho ni Okeru Hotai no Yakuwari to C1qTNF ni yoru Seigyo", The 56th Annual General Assembly and Scientific Meeting of the Japan College of Rheumatology/ The 21st International Rheumatology Symposium, programs, abstracts, Mar. 19, 2012, p. 208.

(Continued)

*Primary Examiner* — Julie Ha
*Assistant Examiner* — Li Ni Komatsu
(74) *Attorney, Agent, or Firm* — Clark G. Sullivan; Troutman Sanders LLP

(57) ABSTRACT

Provided are methods of suppressing complement alternative pathway in a mammalian subject in need thereof, comprising administering to said subject a therapeutically effective amount of C1q and tumor necrosis factor related protein 6 (CTRP6) or a functional analog thereof.

13 Claims, 9 Drawing Sheets

(56) References Cited

OTHER PUBLICATIONS

Japanese Office Action dated Oct. 7, 2014, which issued during prosecution of Japanese Application No. 2013-515089, which corresponds to the present application.
Extended European Search Report for EP 12 78 5351 dated Dec. 10, 2014.
Lee W. et al, "C1qTNF-related protein-6 mediates fatty acid oxidation via the activation of the AMP-activated protein kinase", FEBS Letters, Elsevier, vol. 584, (2010) pp. 968-972.
K. McMahon et al., "The Role of 5'-AMP-Activated Protein Kinase (AMPK) in Diabetic Nephropaty: A New Direction?", Current Enzyme Inhibition, vol. 5, No. 1, 1 (2009) pp. 44-50.
Nath Narender et al, "5-aminoimidazole-4-carboxamide ribonucleoside: a novel immunomodulator in experimental autoimmune encephalomyelitis", Faseb Journal, Fed. of American Soc. For Experimental Biology, US, vol. 19, No. 4, suppl, Mar. 6, 2005, pp. A926-A927.
Lomas H. M. et al., "Targeting AMP-activated protein kinase as a therapeutic strategy for Amyotrophic Lateral Sclerosis", Abstracts of the Annual Meeting of the Society for Neuroscience, Society for Neuroscience, Washington, DC, US, vol. 40, Nov. 17, 2010.
Japanese Office Action dated Feb. 24, 2015, which issued during prosecution of Japanese Application No. 2013-515089, which corresponds to the present application.
S. Nataf, et al., "Attenuation of Experimental Autoimmune Demyelination in Complement-Deficent Mice", The Journal of Immunology, J Immunol 2000; http://www.jimmunol.org/content/165/10/5867.
Lubka T. Roumenina, et al., "Alternative complement pathway assessment in patients with atypical HUS", Journal of Immunological Methods, 365 (2011) pp. 8-26.
Min Chen, et al., "The complement system in systemic autoimmune disease", Journal of Autoimmunity, 34 (2010) pp. J276-J286.
Laura A. Boos, et al., "Murine Complement C4 Is Not Required for Experimental Autoimmune Encephalomyelitis", GLIA 49:158-160 (2004).
Bradley, DT et al., "Complement in age-related macular degenration: a focus on function", Eye (2011) 25, 683,693, www.nature.com/eye.

\* cited by examiner a b

FIGURE 11

Human *C1qtnf6*
ATGCAGTGGCTCAGGGTCCGTGAGTCGCCTGGGGAGGCCACAGGACACAGGGTC
ACCATGGGGACAGCCGCCCTGGGTCCCGTCTGGGCAGCGCTCCTGCTCTTTCTC
CTGATGTGTGAGATCCCTATGGTGGAGCTCACCTTTGACAGAGCTGTGGCCAGC
GGCTGCCAACGGTGCTGTGACTCTGAGGACCCCCTGGATCCTGCCCATGTATCC
TCAGCCTCTTCCTCCGGCCGCCCCCACGCCCTGCCTGAGATCAGACCCTACATT
AATATCACCATCCTGAAGGGTGACAAAGGGGACCCAGGCCCAATGGGCCTGCCA
GGGTACATGGGCAGGGAGGGTCCCCAAGGGGAGCCTGGCCCTCAGGGCAGCAA
GGGTGACAAGGGGGAGATGGGCAGCCCCGGCGCCCCGTGCCAGAAGCGCTTCTT
CGCCTTCTCAGTGGGCCGCAAGACGGCCCTGCACAGCGGCGAGGACTTCCAGAC
GCTGCTCTTCGAAAGGGTCTTTGTGAACCTTGATGGGTGCTTTGACATGGCGACC
GGCCAGTTTGCTGCTCCCCTGCGTGGCATCTACTTCTTCAGCCTCAATGTGCACA
GCTGGAATTACAAGGAGACGTACGTGCACATTATGCATAACCAGAAAGAGGCTGT
CATCCTGTACGCGCAGCCCAGCGAGCGCAGCATCATGCAGAGCCAGAGTGTGAT
GCTGGACCTGGCCTACGGGGACCGCGTCTGGGTGCGGCTCTTCAAGCGCCAGCG
CGAGAACGCCATCTACAGCAACGACTTCGACACCTACATCACCTTCAGCGGCCA
CCTCATCAAGGCCGAGGACGACTGA (SEQ ID NO 25)

Mouse *C1qtnf6*
ATGAGGGTCATCATGGGGATAGCCAGCCTGGGGTTCCTCTGGGCAGTATTCCTG
CTTCCTCTTGTGTTTGGGGTCCCCACAGAGGAGACTACCTTTGGAGAATCTGTGG
CCTCCCATCTCCCCAAAGGCTGTCGACGATGCTGTGACCCCGAGGACCTGATGT
CCTCTGATGATACGGTCCAGGCCCTGTTTCCCCTTATGTCCTGCCTGAAGTCAG
GCCGTACATCAACATTACTATCCTAAAGGGTGACAAAGGGGACAGAGGTCCTACA
GGAACACCAGGGAAGCCAGGCAAGAATGGTACCCGAGGGGACCGTGGCTCTCAG
GGTGTCAAAGGTGACAAGGGGCAGGCAGGTAGCCCTGGCAGCTCGTGCCAGACA
CATTACTCAGCCTTCTCTGTGGGCCGCAAGACTGGCTTGCACAGCAGCGAGAAC
TTCCTCTCACTGCTGTTCGACAGGGTCTTTGTGAACACGGATGGCCACTTTGACA
TGGCCACTGGCAGCTTTGTGGCTCCCCTGCGCGGCCTCTACTTCTTCAGCCTCAA
CGTACACAGCTGGAACTACAAGGAGACCTACGTGCACATCGTGCACAATGAGCA
GGCAGTGGTGATCCTGTACGCGCAGCCCAGCGAACGCAGCATCATGCAGAGCCA
GAGTGTGATGCTGCCACTGGTGCCGGGTGACCGTGTGTGGGTGCGGCTCTTCAA
GCGGGAGCGGGAAAACGGCATCTACAGTGATGACGTGGACACGTACATCACCTT
CAGTGGCCACCTGATCAAGGCAGAGGACAACTGA (SEQ ID NO 27)

CTRP6 WHICH CAN BE USED AS THERAPEUTIC AND PROPHYLACTIC AGENT FOR AUTOIMMUNE DISEASES

CROSS-REFERENCE TO RELATED APPLICATIONS

This application is the U.S. national phase of International Application No. PCT/JP2012/061827 filed May 9, 2012, which claims priority to U.S. Provisional Application No. 61/485,746 filed May 13, 2011 and Japanese Application No. JP 2011-219350 filed Oct. 3, 2011. International Application No. PCT/JP2012/061827 published on Nov. 22, 2012 as Publication No. WO 2012/157479 A1. All of the above applications are incorporated herein by reference in their entirety.

TECHNICAL FIELD

The present invention relates to a pharmaceutical composition containing CTRP6 as an active ingredient. In particular, the present invention relates to the prevention and treatment of autoimmune disease by CTRP6.

BACKGROUND ART

The complement system is an enzyme cascade by serine proteases that mainly assists in defense against infection. The complement system bridges innate immunity and adaptive immunity by amplifying antibody responses and immune memory, lysing foreign cells, removing immune complexes and apoptotic cells, and the like. Many complement components are proteins present as inert zymogens in the serum and play a role in a number of biological functions (chemotactic stimulation, induction of IgE-independent degranulation of mast cells, and the like). Three pathways, the classical pathway, lectin pathway, and alternative pathway, are known in complement activation.

In the classical pathway, the starting point of activation is the interaction of the complement component C1 protein and an antigen-IgM complex or antigen-IgG complex. The lectin pathway (mannose-binding lectin pathway) is activated independent of antibodies by bonding of mannose-binding lectin with mannose groups on the bacterial cell wall, following an activation pathway similar to that of the classical pathway. The alternative pathway is a pathway in which C3 ($H_2O$) produced by adventitious hydrolysis is activated by factor B and factor D. It is spontaneously activated all the time, but is controlled by factor H, factor I, and other such control factors.

All three of the above pathways finally merge into a common pathway. This common pathway begins with C3 convertase cleaving C3 protein into C3a and C3b. The cleavage of C3 promotes the formation of membrane attack complexes that dissolve foreign cells, and the like.

The C1q molecule is the target recognition protein of the classical pathway. The C1q molecule is a heterocomplex constructed from chain A, chain B, and chain C and has a globular domain (gC1q domain) that recognizes the target. Each chain has a short N-terminal region followed by a collagen-like region (CLR), with a gC1q domain located on the C-terminal side of the collagen-like region (Non-patent Reference 1).

Many non-complement proteins having a similar structure to the gC1q domain (also referred to simply as "C1q domain" in this specification) of the C1q molecule are also known. There is a protein group called the C1QTNF superfamily based on the similarity of the tertiary structure of the gC1q domain to TNF. The CTRP (C1QTNF-related protein) family is part of this superfamily as a subfamily especially similar to complement C1q. Seventeen CTRP members have been found in humans.

CTRP1 is a protein discovered as a protein related to the G-protein-coupled receptor. It is expressed mainly in the heart and has a strong anti-troponin effect. CTRP6 and CTRP8 are homologs of CTRP1 and have similar domain structures, but differ in intron-exon pattern. CTRP2 and CTRP7 are thought to belong to the same subfamily based on sequence homology, similarity of domain structure, and intron-exon pattern. CTRP3 is known to promote the differentiation and growth of cartilage cells. CTRP4 alone among this group has one or more C1q domains. CTRP5 was discovered as a protein related to late-onset retinal degeneration and is expressed mainly in the retinal pigment epithelium, liver, lung, brain, and placenta (Patent Reference 1).

Since CTRP1 manifests a strong effect in the prevention of artery blockage and platelet activation, as was mentioned above, and its administration apparently does not induce any bleeding complications, it may be clinically useful in the treatment of various conditions associated with vascular damage, including coronary angioplasty, intimal resection of the carotid artery, and stroke (Patent Reference 2).

However, no relationship between CTRP6 and autoimmune disease due to complement activation is predicted in any of the prior art.

PRIOR ART REFERENCES

Patent References

Patent Reference 1: US Patent Publication No. 2004/0248156A1
Patent Reference 2: Japanese Translation of PCT International Application Publication No. 2008-507591

Non-Patent References

Non-Patent Reference 1: Kishore et al., TRENDS in Immunology, Vol. 25, No. 10, October 2004, pp. 551-561

SUMMARY OF THE INVENTION

Problems to be Solved by the Invention

The object of the present invention is the elucidation of the biological function of CTRP6 and its application.

Means Used to Solve the Above-Mentioned Problems

CTRP6 was clarified to specifically suppress the complement alternative pathway. CTRP6 is therefore a novel inhibitor of the complement alternative pathway. It was also possible to treat arthritis by administration of CTRP6.

Therefore, the present invention relates to (1) a pharmaceutical composition for the prevention or treatment of autoimmune disease containing CTRP6.

It was also possible to treat arthritis in mice using human CTRP6, as in the examples below. It was also discovered that the C1q domains of human CTRP6 and mouse CTRP6 have 82% amino acid sequence identity and that both are involved in suppressing complement activation. Therefore, embodiments of the present invention encompass (2) a pharmaceutical composition according to (1) above wherein CTRP6 comprises an amino acid sequence shown by i) the human CTRP6 sequence (SEQ ID NO: 1) or ii) the mouse CTRP6 sequence (SEQ ID NO: 2);

or is iii) a protein having at least 80% sequence identity with SEQ ID NO: 1 or SEQ ID NO: 2 and activity to suppress complement activation, or iv) a protein comprising an amino acid sequence in which one or several amino acids have been deleted, substituted, or added in the above SEQ ID NO: 1 or SEQ ID NO: 2, and having activity to suppress complement activation.

In relationship to examples of autoimmune diseases appropriately prevented and/or treated by the pharmaceutical composition of the present invention, embodiments of the present invention encompass (3) a pharmaceutical composition according to (1) or (2) above wherein the autoimmune disease is an inflammation selected from the group consisting of rheumatoid arthritis, rheumatoid spondylitis, osteoarthritis, gout, type 1 diabetes, vitiligo, systemic lupus erythematosus, biliary cirrhosis, uveitis, vesicular pemphigoid, Graves' ophthalmopathy, multiple sclerosis, lupus, fibromyalgia, sepsis, septic shock, endotoxin shock, gram-negative bacterial sepsis, toxic shock syndrome, asthma, adult respiratory distress syndrome, chronic obstructive pulmonary disease, chronic pulmonary inflammation, inflammatory bowel disease, Crohn's disease, psoriasis, eczema, ulcerative colitis, pancreatic fibrosis, hepatic fibrosis, acute and chronic nephropathy, irritable bowel syndrome, fever, restenosis, cerebral malaria, ischemic injury, nerve damage, Alzheimer's disease, Huntington's disease, Parkinson's disease, acute and chronic pain, allergic rhinitis, allergic conjunctivitis, chronic heart failure, acute coronary syndrome, and graft-versus-host reaction.

A critical link between CTRP6 and the complement alternative pathway was also demonstrated in the examples below. Therefore, another aspect of the present invention is (4) a pharmaceutical composition according to any of (1) to (3) above wherein the autoimmune disease is a disease related to the complement alternative pathway.

Also provided as an embodiment related to the appropriate use of the present invention is (5) a pharmaceutical composition according to (3) above wherein the autoimmune disease is rheumatoid arthritis or type 1 diabetes.

Advantages of the Invention

The pharmaceutical composition of the present invention can be utilized as an effective drug for the prevention and/or treatment of associated inflammation and autoimmune disease by specifically suppressing the complement alternative pathway or suppressing activation of complement C3.

BRIEF DESCRIPTION OF THE DRAWINGS

FIG. 2b shows the results of Southern blot analysis conducted using a HindIII (restriction site shown by "H" in FIG. 2a) digestion product as a genome probe and a 5' probe (shown as "5' probe" in FIG. 2a) to confirm the production of a C1qtnf6 deletion allele. FIG. 2c shows the results of Southern blot analysis conducted using an EcoRV (restriction site shown by "E" in FIG. 2a) digestion product as a genome probe and a 3' probe (shown as "3' probe" in FIG. 2a) to confirm the production of a C1qtnf6 deletion allele.

In FIGS. 7a-7c, the horizontal axis shows the dilution factor of the serum, and the vertical axis shows the ELISA measurement results on the activated C3b molecule bonded to the plate. The wild type mouse group is listed as "WT" and the knockout mouse group as "KO." The results are expressed by the mean±standard error (both groups, n=8). "" represents a significant difference at a risk of 0.01%, and "*" represents a significant difference at a risk of 0.005% (Student's T-test).

In FIGS. 9a and 9b, the results are expressed by the mean±standard error. "***" represents a significant difference at a risk of 0.005% (Student's T-test). In FIG. 9c, the results are expressed by the mean±standard error, and "*" represents a significant difference at a risk of 0.05% (Mann-Whitney U-test).

FIG. 10a is the results of visual examination from 21 days after the initial immunization by type II collagen (that is, the day of booster immunization). CTRP6 was administered daily from day 28 after the initial immunization. The seriousness score on the vertical axis accorded with the seriousness criteria 0-4 listed in Nat. Protoc. (2007), Vol. 2(5), pp. 1269-1275. The results are expressed by the mean±standard error (n=11). FIG. 10b is a photograph showing the therapeutic effect. Type II collagen was injected at the base of the mouse's tail. The left leg (left side of the photograph) was injected with CTRP6; the right leg (right side of the photograph) was injected with phosphate-buffered physiological saline as a control. In FIG. 10a, the results are expressed by the mean±standard error, and "*" represents a significant difference at a risk of 0.05% (Mann-Whitney U-test).

FIG. 11 shows the base sequences that encode human CTRP6 and mouse CTRP6.

BEST MODE FOR CARRYING OUT THE INVENTION

Figure 1:
FIG. 1 shows the structure of the CTRP6 molecule and the sequence identity of human CTRP6 and mouse CTRP6. The CTRP6 molecule comprises four regions in order from the left of the drawing: a signal peptide, a variable region, a collagen domain, and a C1q domain. The amino acid sequence identity in each region between the human molecule and the mouse molecule is 55, 51, 60, and 82%, respectively.

Any can be used as the active ingredient in the pharmaceutical composition of the present invention as long as it is a protein that manifests CTRP6 activity in vivo. Therefore, these proteins are collectively termed "functional analogs" of CTRP6 in the present invention. One can judge that a certain protein or peptide is a functional analog of CTRP6 by confirming that this protein is capable of specifically suppressing the complement alternative pathway, or that this protein is capable of suppressing complement activation, or both. Concrete examples of this method are listed in the examples as ELISA methods of evaluating complement C3b and/or C5b activation.

Examples discussed below in which mice were treated using human CTRP6 also confirmed that CTRP6 activity has low specificity between species. It is therefore also possible to use a CTRP6 molecule derived from various animals. Furthermore, since the C1q domains of human CTRP6 and mouse CTRP6 have 82% amino acid sequence identity (the maximum is 60% amino acid identity between other domains), those skilled in the art can easily select as functional analogs of CTRP6 those that specifically suppress the complement alternative pathway or suppress complement activation from among proteins or peptides having at least 80% sequence homology with human CTRP6 (SEQ ID NO: 1) or mouse CTRP6 (SEQ ID NO: 2) or having at least about 80% sequence homology with the C1q domain of these CTRP6. Such functional analogs more preferably have at least 85%, 90%, or 95% sequence homology with human CTRP6 (SEQ ID NO: 1) or mouse CTRP6 (SEQ ID NO: 2) or have at least 80%, 90%, or 95% sequence homology with the C1q domain of CTRP6. Furthermore, homology of the amino acid sequence here can be defined as the percentage of positivity shown by the BLASTP algorithm that can be implemented by the internet site <http://www.ncbi.n/m.nih.gov/egi-gin/BLAST> by a search using the default parameters of the program (matrix=Blosum62; gap penalties: existence=11, extension=1).

[Chemical Formula 1]
Human CTRP6:

(SEQ ID NO: 1)

M Q W L R V R E S P G E A T G H R V T M G T A A L G P V W A A L L L F

L L M C E I P M V E L T F D R A V A S G C Q R C C D S E D P L D P A H

V S S A S S S G R P H A L P E I R P Y I N I T I L K G D K G D P G P M

G L P G Y M G R E G P Q G E P G P Q G S K G D K G E M G S P G A P C Q

K R F F A F S V G R K T A L H S G E D F Q T L L F E R V F V N L D G C

F D M A T G Q F A A P L R G I Y F F S L N V H S W N Y K E T Y V H I M

H N Q K E A V I L Y A Q P S E R S I M Q S Q S V M L D L A Y G D R V W

V R L F K R Q R E N A I Y S N D F D T Y I T F S G H L I K A E D D

Mouse CTRP6:

(SEQ ID NO: 2)

M R V I M G I A S L G F L W A V F L L P L V F G V P T E E T T F G E S

V A S H L P K G C R R C C D P E D L M S S D D T V Q A P V S P Y V L P

E V R P Y I N I T I L K G D K G D R G P T G T P G K P G K N G T R G D

R G S Q G V K G D K G Q A G S P G S S C Q T H Y S A F S V G R K T G L

H S S E N F L S L L F D R V F V N T D G H F D M A T G S F V A P L R G

L Y F F S L N V H S W N Y K E T Y V H I V H N E Q A V V I L Y A Q P S

E R S I M Q S Q S V M L P L V P G D R V W V R L F K R E R E N G I Y S

D D V D T Y I T F S G H L I K A E D N

Therefore, those skilled in the art can also easily select as functional analogs of CTRP6 of the present invention those among proteins or peptides consisting of amino acid sequences having one or more amino acids deleted, substituted, or added in the above human CTRP6 (SEQ ID NO: 1) or mouse CTRP6 (SEQ ID NO: 2) that specifically suppress the complement alternative pathway or suppress complement activation as above. In short, these molecules are considered as functional analogs even if they have the structure of one of these molecules but not the other or even if the two amino acid sequences are not completely identical as long as these two molecules have substantially analogous activity. For example, leucine can be substituted by valine, lysine can be substituted by arginine, and glutamine can be substituted by asparagine without changing the function of the polypeptide.

Recombinant human CTRP6 is available as a commercial product (from Bio Vender and Adipo Bioscience). If the desired CTRP6 or functional analog thereof is unavailable, those skilled in the art can prepare such analogs based on the known CTRP6 sequence. For example, since the base sequences that encode human CTRP6 (SEQ ID NO: 1) and mouse CTRP6 (SEQ ID NO: 2) are known (GenBank Accession Numbers: human: CU013002, mouse: BC071187; refer also to FIG. 11), they can be expressed recombinantly by molecular cloning into an expression vector containing a suitable promoter and other suitable transcriptional control elements by utilizing cDNA having this sequence as is or by utilizing DNA that can hybridize with such cDNA under suitable stringent conditions (for example, hybridization by 3×SSC at 68° C., washing by 2×SSC and 0.1% SDS at 68° C.), and transfected into prokaryotic host cells or eukaryotic host cells to produce functional analogs of CTRP6. The techniques of such procedures are described fully by J. Sambrook et al. in Molecular Cloning, A Laboratory Manual $2^{nd}$ ed., Cold Springs Harbor Laboratory, New York (1989) and are known to those skilled in the art.

The method of administration of the pharmaceutical composition of the present invention may be either systemic or local. Examples of systemic administration include oral administration and parenteral administration, including subcutaneous administration, intraperitoneal administration, intramuscular injection, intra-arterial administration, and intravenous administration, and the like. Examples of local administration include local injection to the epidermis, eye, and various tumors, administration to the lungs and bronchi by inhalation of aerosol, and the like. The dose of the pharmaceutical composition of the present invention varies depending on the patient's age, physique, gender, severity of symptoms, specific activity of the active ingredient, pharmaceutical form, and other such factors. For example, the effective dose of human CRP6 used as an intramuscular injection is 0.01 µg to 10 mg/kg/day, preferably 0.1-500 µg/kg/day, and more preferably 1-50 µg/kg/day. The dose may be adjusted as is appropriate to match the patient's condition and the inflammation or disease to be treated. Furthermore, the frequency of administration may be 1-2 times/day, or daily, or 1-3 times/week.

Pharmacologically acceptable additives can be contained together with the CTRP6 or functional analog thereof used in the present invention in the pharmaceutical composition of the present invention. For example, in a composition in the form of an injectable preparation, pH buffer, preservative, and isotonifying agent can be added as needed. Those having a pH buffering effect that can be added to injectable preparations are used as pH buffers. Examples include acetic acid, succinic acid, tartaric acid, lactic acid, or salts thereof, or the like. Methyl p-oxybenzoate, ethyl p-oxybenzoate, propyl p-oxybenzoate, and other such parabens; 2-phenylethanol, ethyl alcohol, chlorobutanol, and other such alcohols; benzalkonium chloride, benzethonium chloride, cetyl pyridinium chloride, and other such surfactants may be added as preservatives. Sodium chloride, potassium chloride, and other such inorganic salts, monosaccharides, disaccharides, and other such sugars can be used as isotonifying agents as long as they are common pharmacologically acceptable ones.

The pharmaceutical composition of the present invention can be used advantageously for the prevention and/or treatment of autoimmune disease. The complement alternative pathway is a cascade activated by deposition of C3b on a sensitive surface. This pathway is activated via inflammatory activity including activation of mast cells, macrophages, neutrophils, endothelial cells, and the like and tissue damage and forms C5b-9 complexes, which are membrane attack complexes, on the sensitive surface and damages cells together with producing biologically active fragments of complement proteins such as C3a, C4a, C5a anaphylatoxin, and the like. Consequently, it is reasonable to expect that suppressing activation of the complement alternative pathway will make it possible to prevent and treat a wide range of autoimmune diseases.

Model animal experiments on suppression of complement activation report that it can be effective in the treatment of rheumatoid arthritis (Y. Wang et al., Proc. Natl. Acad. Sci. (1995), Vol. 92, pp. 8955-8959), systemic lupus erythematosus and glomerulonephritis (Y. Wang et al., Proc. Natl. Acad. Sci. (1996), Vol. 93, pp. 8563-8568), reperfusion injury (E. A. Amsterdam et al., Am. J. Physiol. (1995), Vol. 268, pp. H448-H457), adult respiratory distress syndrome (R. Rabinovici et al., J. Immunol. (1992), Vol. 49, pp. 1744-1750), cardiopulmonary bypass and hemodialysis (C. S. Rinder, J. Clin. Invest. (1995), Vol. 96, pp. 1564-1572), myocardial infarction (J. W. Homeister et al., J. Immunol. (1993), Vol. 150, pp. 1055-1064; H. F. Weisman et al., Science (1990), Vol. 249, pp. 146-151), and hyperacute rejection in organ transplant (T. J. Kroshus et al., Transplantation (1995), Vol. 60, pp. 1194-1202). Burns, severe asthma, anaphylactic shock, inflammation of the bowel, hives, vascular edema, angiitis, multiple sclerosis, myasthenia gravis, membranoproliferative glomerulonephritis, and other such inflammatory symptoms and autoimmune/immune complex diseases are also intimately related to complement activation (V. M. Holers, Clinical Immunology, Principles and Practice (book), edited by R. R. Rich, published by Mosby Press, 1996, pp. 363-391; B. P. Morgan, Eur. J. Clin. Invest. (1994), Vol. 24, pp. 219-228). WO2007/103549 discloses a method of treating and/or preventing uveitis, allergic conjunctivitis, and other such complement-mediated eye disorders by suppressing complement activation. WO2004/103294 discloses methods of preventing and treating sepsis and septic shock by a complement inhibitor. WO2006/101860 mentions that inhibitors of the complement cascade can be useful in the treatment of neurodegenerative diseases, including Alzheimer's disease. Therefore, examples of autoimmune diseases and associated inflammatory symptoms that can be prevented and treated by the pharmaceutical composition of the present invention are rheumatoid arthritis, rheumatoid spondylitis, osteoarthritis, gout, type 1 diabetes, vitiligo, systemic lupus erythematosus, biliary cirrhosis, uveitis, vesicular pemphigoid, Graves' ophthalmopathy, multiple sclerosis, lupus, fibromyalgia, sepsis, septic shock, endotoxin shock, gram-negative bacterial sepsis, toxic shock syndrome, asthma, adult respiratory distress syndrome, chronic obstructive pulmonary disease, chronic pulmonary inflammation, inflammatory bowel disease, Crohn's disease, psoriasis, eczema, ulcerative colitis, pancreatic fibrosis, hepatic fibrosis, acute and chronic nephropathy, irritable bowel syndrome, fever, restenosis, cerebral malaria, ischemic injury, nerve damage, Alzheimer's disease, Huntington's disease, Parkinson's disease, acute and chronic pain, allergic rhinitis, allergic conjunctivitis, chronic heart failure, acute coronary syndrome, and graft-versus-host reaction.

In particular, as in the examples below, the CTRP6 of the present invention suppressed activation of the complement alternative pathway and also suppressed deposition of complement C3b and formation of C5b-9 complexes. Therefore, the prevention/treatment of autoimmune diseases and associated inflammation related to the complement alternative pathway, specifically rheumatoid arthritis or type 1 diabetes, is a very interesting phenomenon, but is not limited to this.

The pharmaceutical composition of the present invention can be used in combination with other anti-inflammatories and analgesics as long as this does not cause any serious adverse effects in the patient. For example, it can be used in combination with 5-lipoxygenase inhibitors, cyclooxygenase-2 inhibitors, interleukin-1 inhibitors, NMDA antagonists and nitric oxide inhibitors or nitric oxide synthesis inhibitors, nonsteroidal anti-inflammatories or cytokine-suppressive anti-inflammatories.

(1) The fact that arthritis exacerbated significantly in C1qtnf6 KO mice in comparison to wild type (WT) mice as a result of creating C1qtnf6 (CTRP6 gene) KO mice and inducing collagen-induced arthritis, (2) the fact that CTRP6 specifically suppressed the complement alternative pathway, (3) the fact that C1qtnf6 Tg mice (mice that overexpress CTRP6) were created and symptoms of arthritis improved in these mice, and (4) the fact that arthritis in mice can be treated by administration of human CTRP6 are explained in detail below based on examples. Nonetheless, it goes without saying that the present invention is not limited to the examples.

EXAMPLES

Example 1

Arthritis Exacerbates in C1qtnf6 KO Mice 1-a. Production of C1qtnf6 KO Mice

Exon 3 that encodes the C1q domain of the C1qtnf6 gene was substituted by a neomycin resistance gene (Neo$^r$) by homologous recombination in E14.1 ES cells. A diphtheria toxin gene (DT) was also bonded to the 3' terminal of the genome fragment for negative selection.

Specifically, genomic DNA corresponding to C1qtnf6 was amplified from the genomic DNA of E14.1 ES cells using the following primers.

[Chemical Formula 2]
5' arm (SEQ ID NO: 3)
Sense:      5'-tccccgcggctccaaaccatgctgactct-3'

(SEQ ID NO: 4)
Antisense:  5'-cgtctagaagcacctaactgcatgctgg-3'

3' arm (SEQ ID NO: 5)
Sense:      5'-ccatcgatatctgggcaagtccccatgtct-3'

(SEQ ID NO: 6)
Antisense:  5'-acgcgtcgactcctcctgggtcattctgca-3'

Fragments of 3.5 kb and 6.9 kb, respectively, were obtained as the 5' and 3' arms by this amplification.

A targeting vector was constructed by substituting the genomic fragment corresponding to exon 3 (encoding the C1q domain) of the C1qtnf6 gene by a DNA fragment containing a neomycin resistance gene (Neo$^r$) under PGK1 promoter control for positive selection. A diphtheria toxin gene (DT) under MC1 promoter control was also bonded to the 3' terminal of this targeting vector for negative selection. A stop codon and a HindIII sequence for screening were also introduced into exon 2 of this targeting vector (see FIG. 2). The targeting vector constructed in this way was introduced into ES cells (E14.1) by electroporation and selected by G418 (manufactured by Nacalai). The target clones were screened by PCR and Southern blot hybridization analysis. The first screening was conducted by PCR using the following primers.

[Chemical Formula 3]
```
                                            (SEQ ID NO: 7)
Sense:      5'-ctctttctggcaagcacatagctc-3'

(SEQ ID NO: 8)
Antisense:  5'-agaggaacccaagcttcttacagg-3'
```

The target clones were confirmed by continuing the above PCR screening and conducting Southern blot hybridization analysis. Specifically, the genome of the ES cells was digested by HindIII and EcoRV and used as 5' and 3' probes, respectively. In brief, the 5' probe was amplified by the following primers.

[Chemical Formula 4]
```
                                            (SEQ ID NO: 9)
Sense:      5'-aacctgacttatgtgtgggcag-3'

(SEQ ID NO: 10)
Antisense:  5'-caggattgtatgagtgtctggg-3'
```

The 3' probe was amplified by the following primers.

[Chemical Formula 5]
```
                                            (SEQ ID NO: 11)
Sense:      5'-agaggatgtgtgcgtagtccaa-3'

(SEQ ID NO: 12)
Antisense:  5'-tggatggacagatggatggatg-3'
```

One target cell was identified as a result of the above screening (targeting efficiency 0.5%). Chimeric mice were created by a condensation method in accordance with the literature (Proc. Natl. Acad. Sci. USA, Vol. 90, pp. 8424-8428 and J. Exp. Med., Vol. 187, pp. 1463-1475) using this target clone. The contribution of the ES cells to these chimeric mice was confirmed by the coat color. Next, male chimeric mice were mated with female C57BL/6J mice to create heterozygous progeny. The F1 progeny were crossed, and heterozygous C1qtnf6 KO mice were obtained. Furthermore, C1qtnf6 KO mice of the same litter of F1 (C57BL/6J×12901a/Hsd) background were used in type II collagen (sometimes abbreviated hereinafter as "IIC") restimulation assay and complement assay (detection of C5b-9), and mice of C57BL/6 background were used in other studies in the examples below. The following primers were used in genotyping of the C1qtnf6 KO mice.

[Chemical Formula 6]
```
WT sense:
                                            (SEQ ID NO: 13)
            5'-ggcatctctggtgcttacaaccaag-3'

Mutant sense:
                                            (SEQ ID NO: 14)
            5'-agttatacgcgttcgctcggtaccca-3'

Antisense (common):
                                            (SEQ ID NO: 15)
            5'-gacagcaagctgatcatccacactca-3'
```

Figure 2:
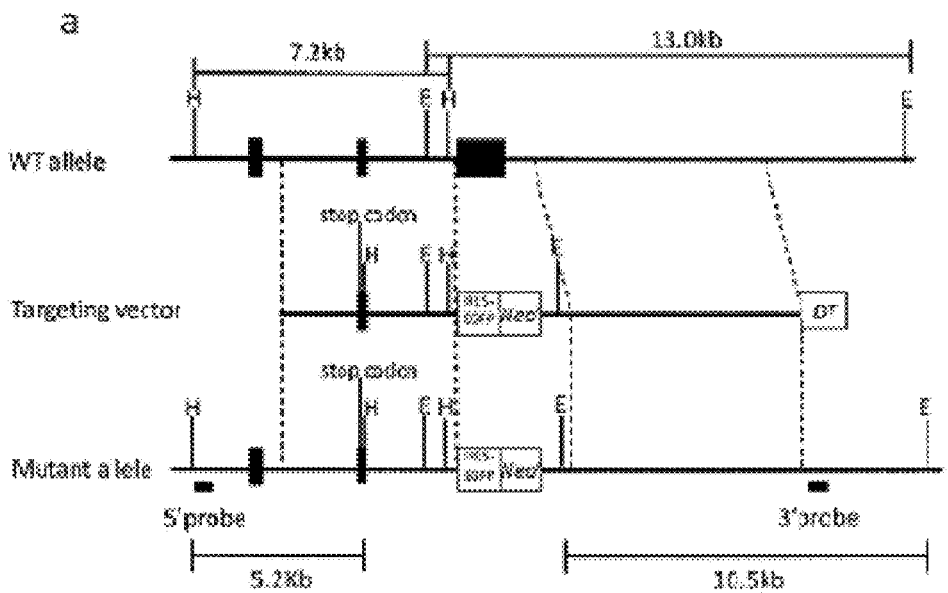
FIG. 2 The upper part of FIG. 2a shows the wild type (WT) allele structure of mouse C1qtnf6, the middle part shows the structure of the targeting vector, and the lower part shows the predicted structure of a mutant allele of C1qtnf6. In the figure, exons are represented by filled rectangles. Exon 3 of the C1qtnf6 gene encoding the C1q domain is substituted by a neomycin resistance gene (Neo$^r$). A diphtheria toxin gene (DT) was bonded to the 3' terminal of the genome fragment for negative selection.
Figure 2:
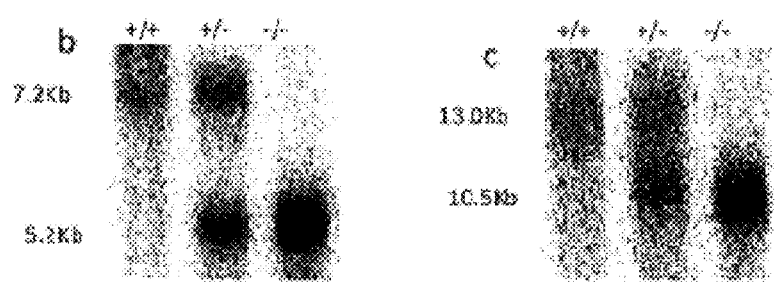

The above common antisense primer and WT sense primer were used in detection of the WT allele (686 bp), and the common antisense primer and mutant sense primer were used in detection of the mutant allele (454 bp) (see FIG. 2).

1-b. Arthritis Exacerbates in C1qtnf6 KO Mice

The exacerbation of collagen-induced arthritis (CIA) in C1qtnf6 KO mice was tested by the following method.

Figure 3:
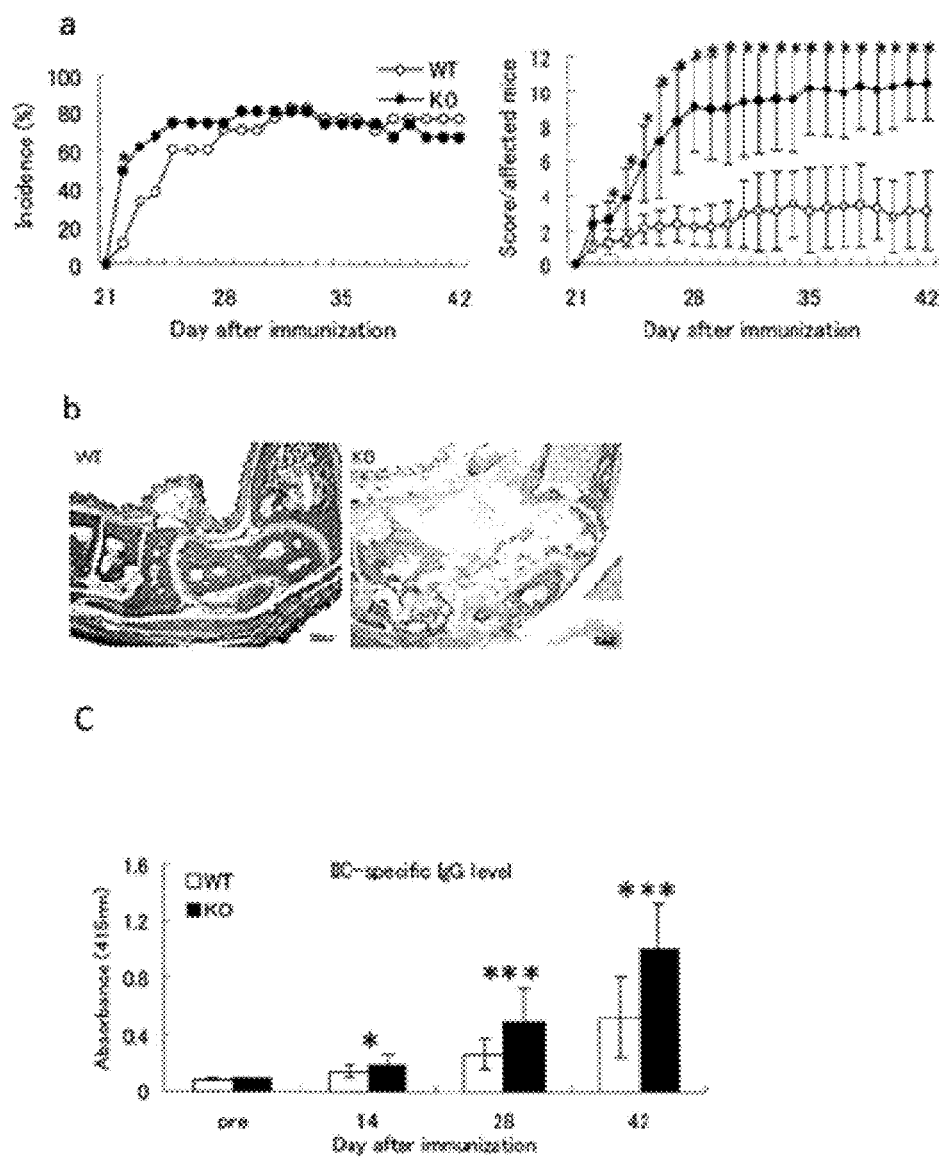
FIG. 3a shows the results obtained by comparing the exacerbation (*2) of collagen-induced arthritis between C1qtnf6 knockout mice (shown by "KO") and wild type mice (shown by "WT"). The left side of FIG. 3a shows the incidence (vertical axis: Incidence (%)) of arthritis. The right side shows the seriousness (horizontal axis: Score/affected mice) evaluated from 21 days after the first immunization by type II collagen (that is, the day of booster immunization). The incidence and seriousness score accorded with the standards listed in Nat. Protoc. (2008), Vol. 3(4), pp. 612-618. The results are expressed by the mean±standard error (WT: n=18 and KO: n=16 by total of two independent studies). "*" represents a significant difference at a risk of 0.05% (Mann-Whitney U-test).
FIG. 3b shows the results of histopathological studies of the mouse joints 42 days after the initial immunization. Typical symptoms of synovitis are seen in the affected joints (right side of FIG. 3b) of KO mice. The scale bar in the photographs corresponds to 300 µm.
FIG. 3c shows the results obtained by detecting the type II collagen (IIC)-specific IgG level in mouse serum by ELISA before the initial immunization ("pre" on the horizontal axis of the figure) and 14, 28, and 42 days after the initial immunization. The results are expressed by the mean±standard error (WT: n=18 and KO: n=16 by total of two independent studies). "*" represents a significant difference at a risk of 0.05% and "***" represents a significant difference at a risk of 0.005% (Student's T-test).

Using a liquid obtained by emulsifying type II collagen (manufactured by Sigma) in a concentration of 2 mg/mL and heat-killed *Mycobacterium tuberculosis* (H37Ra; manufactured by Difco) in a concentration of 1.65 mg/mL relative to incomplete Freund adjuvant (IFA; manufactured by Difco), an initial immunization (day 0) was performed by subcutaneous injection of 100 μL of this emulsified liquid at three locations near the base of the mouse's tail. Booster immunization was performed on day 21. In this case, 100 μL of liquid obtained by emulsifying the same amount of type II collagen (IIC) as above with complete Freund adjuvant was injected subcutaneously in the above mice near the locations of the previous injections. The incidence of arthritis and seriousness scores in these mice were subsequently evaluated by the criteria stated in Nat. Protoc. (2008), Vol. 3(4), pp. 612-618. Furthermore, the studies were conducted twice independently (total number of animals in the two studies: WT: n=18, KO: n=16). Histopathology studies of the joints were also conducted 42 days (day 42) after the initial immunization. Serum was also collected from the mice before and after the initial immunization, and the IIC-specific IgG level was studied by ELISA. The results are shown in FIG. 3.

As shown in FIG. 3a, arthritis exacerbated significantly in C1qtnf6 KO mice (sometimes abbreviated hereinafter as "KO mice"). As far as the histopathology findings, FIG. 3b shows that typical synovitis developed in the joints of the KO mice. FIG. 3c also shows that elevation of the IIC-specific IgG level after the initial immunization was significantly greater in the KO mice than in the WT mice.

1-c. CTRP6 Does not Affect Antibody Production by B Cells

Thymus-dependent (or -independent) antibody production was tested by the following method.

To evaluate the immune response to thymus-dependent antigen, C1qtnf6 KO mice were immunized by intraperitoneal injection of a mixture of 200 μg of trinitrophenyl 16 [TNP(16)]-keyhole limpet hemocyanin (KLH) (manufactured by Biosearch Technologies) and the same amount of Imject Alum (trade name; manufactured by Pierce). Booster immunization was performed on day 21. Serum was collected at the time of the initial immunization (day 0) and days 14 and 30 thereafter, and the TNP-KLH-specific IgG1 level was assayed by ELISA. In ELISA, collected serum that had been diluted to 1:500 served as the test sample, and the TNP-specific antibody level of the sample was measured using a plate coated by 20 μg of TNP(30)-BSA and a conjugate of alkaline phosphate and goat and rabbit polyclonal antibody to mouse IgG1 (manufactured by Zymed).

Figure 4:
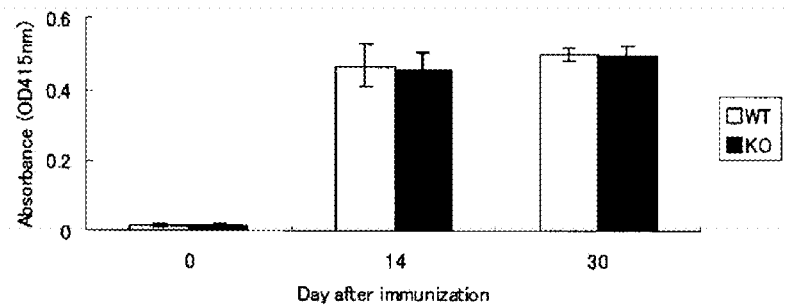
FIG. 4a shows the results obtained by detecting the TNP-KLH-specific IgG1 level in mouse serum by ELISA on days 0, 14, and 30 after the initial immunization. The results are expressed by the mean±standard error (both groups, n=10).
FIG. 4b shows the results obtained by detecting the TNP-Ficoll-specific IgG3 level in mouse serum by ELISA on days 0 and 7 after the initial immunization. The results are expressed by the mean±standard error (both groups, n=9). The wild type mouse group is listed as "WT" and the knockout mouse group as "KO" in both FIGS. 4a and 4b.
Figure 4:
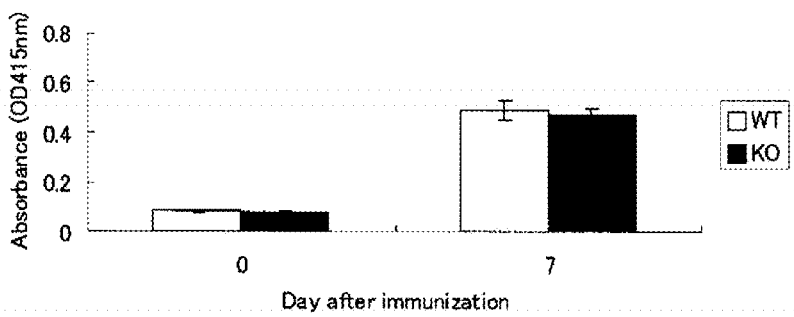

On the other hand, to evaluate the immune response to thymus-independent antigen, C1qtnf6 KO mice were immunized by intraperitoneal injection of 200 μg of trinitrophenyl 65-aminoethyl-carboxyl-methyl (AECM)-Ficoll (manufactured by Biosearch Technologies). Serum was collected seven days after immunization, and the TNP-Ficoll-specific IgG3 level was assayed. In this assay, the above serum that had been diluted to 1:100 served as the sample, and the TNP-specific antibody level was determined by ELISA using a plate coated by 20 μg of TNP(30)-BSA and a conjugate of alkaline phosphate and goat and rabbit polyclonal antibody to mouse IgG3 (manufactured by Zymed). Both FIGS. 4a and 4b show that CTRP6 did not affect antibody production by B cells.

Figure 5:
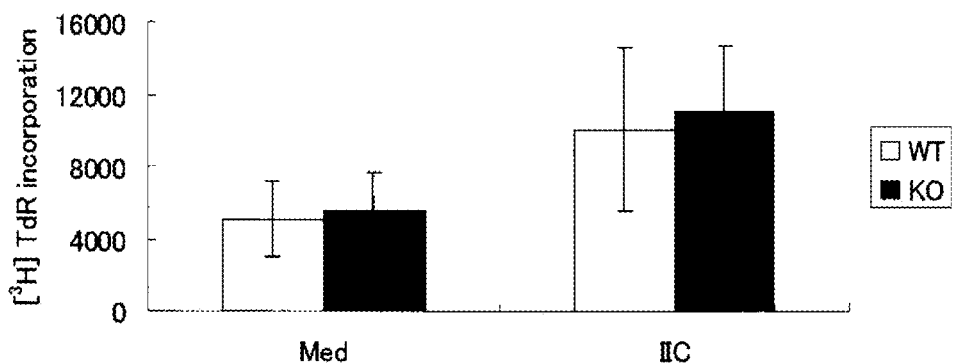
FIG. 5 is a graph showing lymphocyte proliferation when lymphocytes collected from mice on day 7 after the initial immunization were cultured with (expressed as "IIC" in the figure) or without (expressed as "Med" in the figure) type II collagen present as [$^3$H]TdR uptake. The wild type mouse group is listed as "WT" and the knockout mouse group as "KO." The results are expressed by the mean±standard error (both groups, n=6).

1-c'. The Proliferative Response of Lymph Node Cells to Antigen is Also Normal in C1qtnf6 KO Mice 12901a/Hsd×C57BL/6J F1 mice were immunized using 100 μL of liquid obtained by emulsifying IIC in a concentration of 2 mg/mL and heat-killed *Mycobacterium tuberculosis* (H37Ra; manufactured by Difco) in a concentration of 5 mg/mL with complete Freund adjuvant (CFA; manufactured by Difco). Lymph node cells were collected on day 7 after immunization. The collected lymph node cells ($5 \times 10^5$ cells/well) were cultured for three days with or without 100 mg/mL of heat-denatured IIC present. [$^3$H]TdR (0.25 mCi/mL) was caused to be taken up by the cells from six hours before the end of culture. As shown in FIG. 5, the proliferative response of lymph node cells to antigen was the same in C1qtnf6 KO mice as in WT mice, and the mice responded normally.

1-d. Complement C3a Increased in C1qtnf6 KO Mice

Figure 6:
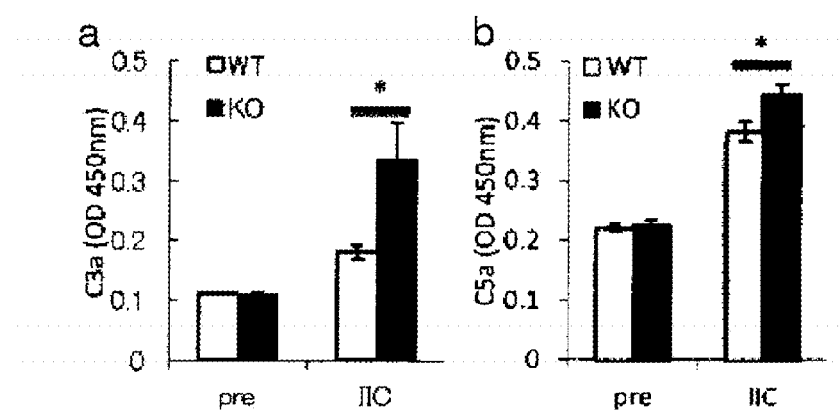
FIG. 6a shows the results obtained by detecting the complement C3a molecule in mouse plasma by ELISA before the initial immunization and on day 7 after the initial immunization.
FIG. 6b shows the results obtained by detecting the complement C5a molecule in the serum by ELISA before the initial immunization and on day 7 after the initial immunization. In both FIGS. 6a and 6b, "pre" on the horizontal axis shows the data from before the initial immunization and "IIC" shows the data from day 7 after the initial immunization by type II collagen. The wild type mouse group is listed as "WT" and the knockout mouse group as "KO." The results are expressed by the mean±standard error (both groups, n=8). "*" represents a significant difference at a risk of 0.05% (Student's T-test).

Using a liquid obtained by emulsifying type II collagen (manufactured by Sigma) in a concentration of 2 mg/mL and heat-killed *Mycobacterium tuberculosis* (H37Ra; manufactured by Difco) in a concentration of 1.65 mg/mL relative to incomplete Freund adjuvant (IFA; manufactured by Difco), immunization was performed by subcutaneous injection of 100 μL of this emulsified liquid at three locations near the base of the mouse's tail. Plasma was collected from the mice on day 7 after immunization by type II collagen (IIC). The plasma was incubated in a plate (manufactured by BD Falcon) coated by anti-mouse C3a capture monoclonal antibody or anti-mouse C5a capture monoclonal antibody (both manufactured by BD Pharmigen), and the complement C3a and complement C5a in the mouse plasma were detected using biotin-conjugated detection monoclonal antibody (manufactured by BD Pharmigen) (n=8). As shown in FIG. 6, the production of the complement C3a and C5a molecules was significantly elevated in comparison to WT mice after IIC stimulation in C1qtnf6 KO mice.

1-e. The Complement Alternative Pathway Activates Specifically in C1qtnf6 KO Mice Plates (manufactured by Nunc) were coated by OVA/anti-OVA immune complex (OVA; manufactured by Sigma, anti-OVA antibody; manufactured by Millipore), 50 μg/mL of mannan (manufactured by Sigma), and 200 μg/mL of LPS (manufactured by Sigma), respectively, to assay complement activation of the classical pathway (CP), lectin pathway (LP), and alternative pathway (AP) by a method in accordance with Blood (Jan. 15, 2008), Vol. 111(2), pp. 732-740) (Epub Oct. 4, 2007). Serum collected from normally raised mice (n=8) diluted to 1, 2, and 4% and serum-free solution were incubated for one hour at 37° C. in the plates, and the activated C3b bonded to the plates was then assayed using anti-mouse C3 antibody (manufactured by abeam). The CP and LP activity were assayed in GVB2+ buffer, and the AP activity was assayed in GVB/MgEGTA buffer.

Figure 7:
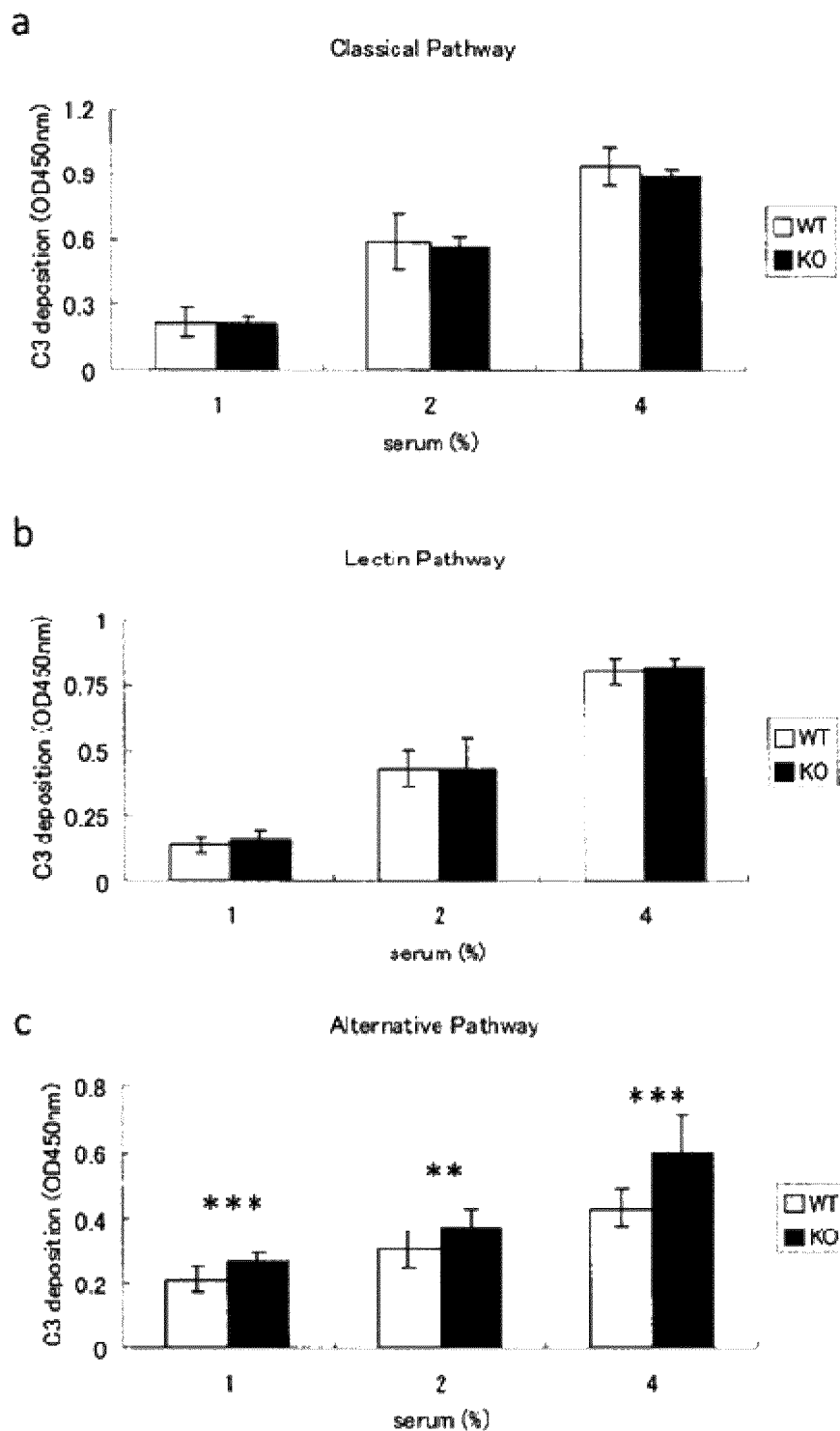
FIG. 7a shows the results obtained by measuring activation of the complement classical pathway in serum collected from normally raised mice as deposition of the complement C3b molecule.
FIG. 7b shows the results obtained by measuring activation of the complement lectin pathway in serum collected from normally raised mice as deposition of the C3b molecule.
FIG. 7c shows the results obtained by measuring activation of the complement alternative pathway in serum collected from normally raised mice as deposition of the complement C3b molecule.

In brief, as shown in FIG. 7, only the alternative pathway (AP) was judged to activate readily in KO mice as a result of studying the activation of the three pathways, the classical pathway (CP), lectin pathway (LP), and alternative pathway (AP), by reacting serum under different plate conditions and buffer conditions.

Example 2

CTRP6 Suppresses Activation of the Complement Alternative Pathway Concentration-Dependently It was judged based on 1-e. above that only the alternative pathway (AP) activates readily in KO mice.

Therefore, as a reconstitution experiment, various concentrations of recombinant CTRP6 (available from Bio Vender) were mixed in advance with C1qtnf6 KO mouse serum (5%) in GVB/MgEGTA buffer, and the AP activity was assayed by the procedure of 1-e. above. Here, various concentrations of CTRP6 were also mixed with KO mouse serum (10%) in advance, and the formation of C5b-9 complexes was assayed by an anti-mouse C5b-9 antibody (abcam) protocol using plates with LPS immobilized in a concentration of 200 μg/mL.

Figure 8:
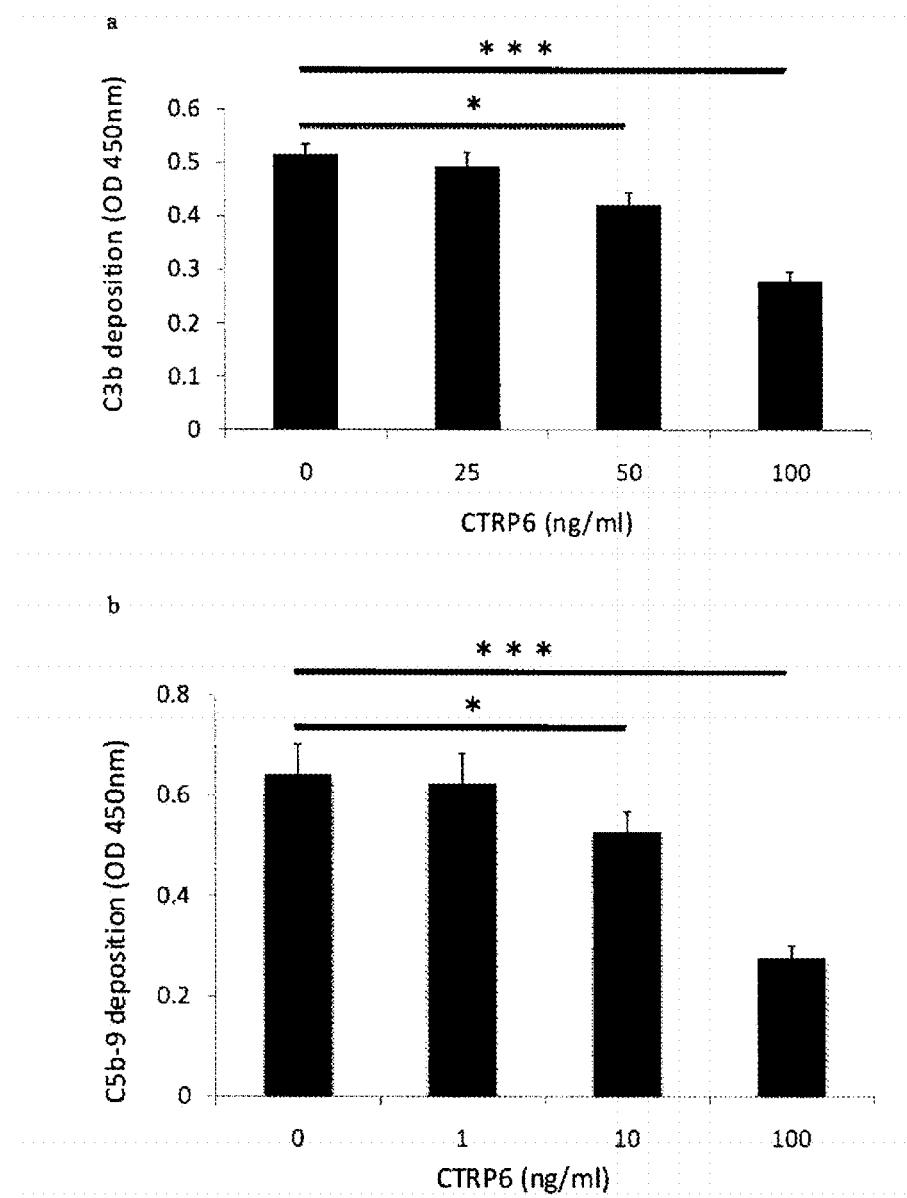
FIG. 8a shows the results obtained by measuring activation of the complement alternative pathway as deposition of the complement C3b molecule when various concentrations of CTRP6 molecule were added in advance to serum (5% diluted) collected from normally raised C1qtnf6 KO mice.
FIG. 8b shows the results obtained by measuring activation of the complement alternative pathway as deposition of complement C5b-9 complex when various concentrations of CTRP6 molecule were added in advance to serum (10% diluted) collected from normally raised C1qtnf6 KO mice. In both FIGS. 8a and 8b, the horizontal axis shows the CTRP6 concentration added, and the vertical axis shows the ELISA measurement results of activated C3b molecule or C5b-9 complex bonded to the plate. The results are expressed by the mean±standard error (both groups, n=8). "*" represents a significant difference at a risk of 0.05%, and "***" represents a significant difference at a risk of 0.005% (Student's T-test).

As shown in FIGS. 8a and 8b, concentration-dependent suppression of the alternative pathway by CTRP6 was confirmed as suppression of activation of complement C3b and complement C5b, respectively, as a result of varying the concentration (5% and 10%) of serum of KO mice that do not produce CTRP6 and adding CTRP6.

Example 3

Arthritis was Suppressed by Overexpression of CTRP6

3-a. Production of C1qtnf6 Tg Mice

C1qtnf6 Tg mice (mice that overexpress CTRP6) were created as follows. Refer to Example 1-a. for the details.

Mouse C1qtnf6 (full length) cDNA amplified by RT-PCR using the following primers was incorporated downstream of a CAG promoter in a pCXN vector.

```
[Chemical Formula 7]
RT-PCR primers
                                    (SEQ ID NO: 16)
Sense:     5'-TTGAATTCGCAGGATGAGGGTCATCATGG-3'

(SEQ ID NO: 17)
Antisense: 5'-CGGAATTCAGTTGTCCTCTGCCTTGATC-3'
```

The amplified cDNA fragment was sequenced and confirmed to be the correct sequence. After introducing this cDNA fragment into a vector, the vector was treated by BamHI and PvuI, and a purified fragment was obtained. The fragment purified in this way was microinjected into the pronuclei of eggs of C57BL/6J mice, and the eggs were placed in the oviducts of pseudopregnant ICR mice. Whether or not the mice obtained were Tg mice was confirmed by PCR using the following primers, and the genomic DNA was treated by HindIII and EcoRI and confirmed by Southern blotting.

```
[Chemical Formula 8]
PCR confirmation primer
                                    (SEQ ID NO: 18)
Sense:     5'-ACGTGCTGGTTGTTGTGCTGTCTC-3'
```

```
                                                            (SEQ ID: 19)
Antisense:      5'-CTTTATAGCCACCTTTGTTCATGGC-3'

Southern blotting confirmation primer
                                                            (SEQ ID NO: 20)
Sense:          5'-CTACAGGAACACCAGGGAAGCCA-3'

(SEQ ID NO: 21)
Antisense:      5'-TTGATCAGGTGGCCACTGAAGGT-3'
```

The following three primers were used in genotyping of the Tg mice.

```
[Chemical Formula 9]
                                                            (SEQ ID NO: 22)
Common:         5'-CTGTGTACGTTGAGGCTGAAGAAG-3'

(SEQ ID NO: 23)
WT-specific:    5'-TGGCCTCAGTTTCACTTCTGCAGA-3'

(SEQ ID NO: 24)
Tg-specific:    5'-ATCCTAAAGGGTGACAAAGGGGAC-3'
```

Littermates were also used in the study.

3-b. Arthritis is Suppressed in C1qtnf6 Tg Mice

1) The CTRP6 in the plasma of the C1qtnf6 Tg mice (sometimes abbreviated as Tg mice) created in this way was confirmed by ELISA. Specifically, mouse serum diluted to 10% was incubated for one hour at room temperature in plates (manufactured by Nunc) coated by anti-CTRP6 antibody (manufactured by Anaspec), and the amount of CTRP6 bonded to the plate was then determined using biotinized anti-CTRP6 antibody (antibody manufactured by Anaspec biotinized using a Dojindo Labeling Kit (manufactured by Cosmo Bio)).

Figure 9:
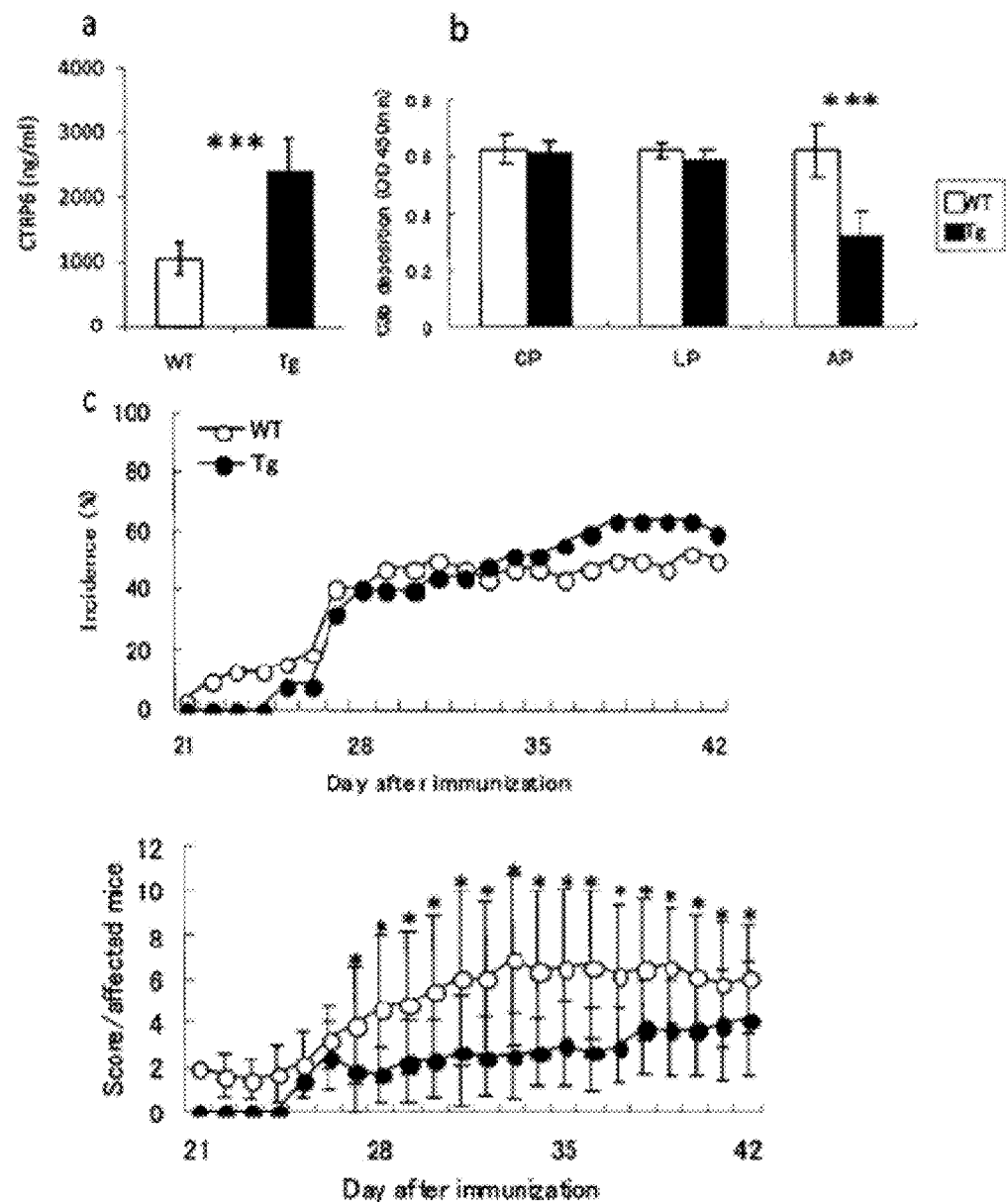
FIG. 9a shows the results obtained by confirming the CTRP6 level in the plasma of C1qtnf6 Tg mice (n=8) by ELISA. The vertical axis represents the CTRP value (ng/mL).
FIG. 9b shows the results obtained by measuring activation of the complement classical pathway (CP), lectin pathway (LP), and alternative pathway (AP) in serum collected from normally raised C1qtnf6 Tg mice (n=5) as deposition of the complement C3b molecule. The vertical axis represents the ELISA measurement results on activated C3b molecule bonded to the plate.
FIG. 9c shows the results obtained by comparing exacerbation (*2) of collagen-induced arthritis between C1qtnf6 Tg mice (shown by "Tg") and wild type mice (shown by "WT"). The upper part of FIG. 9c is the incidence of arthritis (vertical axis: Incidence (%)) and the lower part is the seriousness (vertical axis: Score/affected mice) evaluated from 21 days after the initial immunization by type II collagen (that is, the day of booster immunization). The incidence and seriousness score accorded with the standards listed in Nat. Protoc. (2008), Vol. 3(4), pp. 612-618. WT: n=32 and Tg: n=25 by total of two independent studies.

The results are shown in FIG. 9a. As intended, the amount of CTRP6 in the C1qtnf6 Tg mouse plasma was significantly greater than in WT.

2) Next, suppression of collagen-induced arthritis (CIA) in C1qtnf6 Tg mice was tested by the procedure of 1-b. above. However, the concentration of heat-killed *Mycobacterium tuberculosis* (H37Ra; manufactured by Difco) in the emulsified liquid used in immunization was set at 2.5 mg/mL to make the symptoms more serious than in the study in WT by increasing the amount of killed *Mycobacterium tuberculosis*.

As shown in FIG. 9c, exacerbation of arthritis in C1qtnf6 Tg mice was significantly suppressed in comparison to WT.

3) The fact that the complement alternative pathway is specifically suppressed in C1qtnf6 Tg mice was also verified by the procedure of 1-e. above.

The results in FIG. 9b confirmed that the complement alternative pathway is specifically suppressed in C1qtnf6 Tg mice.

Example 4

Arthritis can be Treated by Administration of CTRP6

An animal model of arthritis was produced based on DBA/1J mice. Using a liquid obtained by emulsifying type II collagen in a concentration of 2 mg/mL relative to complete Freund adjuvant (CFA; manufactured by Difco), an initial immunization (day 0) was performed by subcutaneous injection of 100 µL of this emulsified liquid at three locations near the base of the mouse's tail. Booster immunization was performed on day 21. In this case, 100 µL of liquid obtained by emulsifying the same amount of type II collagen (IIC) as above with complete Freund adjuvant was injected subcutaneously in the above mice near the locations of the previous injections.

To test the effect of CTRP6 on arthritis, recombinant human CTRP6 solution (corresponding to 300 ng of CTRP6) obtained from Adipo Bioscience and PBS (pH 7.4) from day 28, each in an injection quantity of 30 µL, were injected into the articular cavity of the knee joint, CTRP6 to the left leg and PBS to the right leg, of the DBA/1J mice (n=11).

Swelling and reddening of the joint were examined visually thereafter in the left and right legs and evaluated on a seriousness scale of 0-4 described in Nat. Protoc. (2007), Vol. 2(5), pp. 1269-1275.

Figure 10:
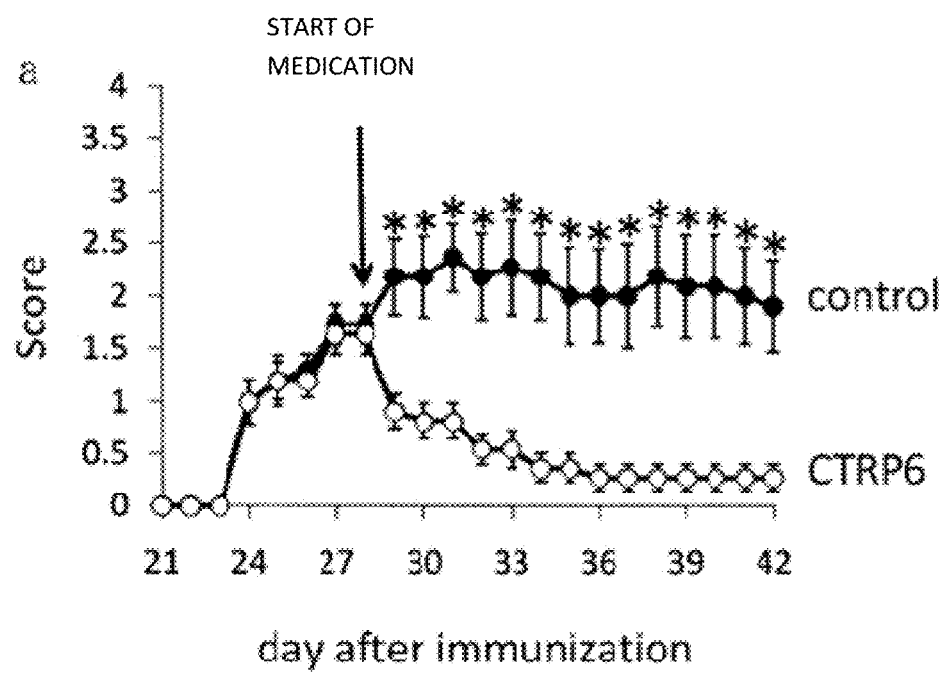
FIG. 10 shows the therapeutic effect of human CTRP6 in DBA/1J mice in which collagen-induced arthritis was induced by immunization by type II collagen.
Figure 10:

The results in FIG. 10 clearly showed that CTRP6 administration to DBA/1J mice that had developed arthritis improved the symptoms of the arthritis. In addition, the left leg injected with CTRP6 was healed in 8 of 11 mice.

INDUSTRIAL APPLICABILITY

A pharmaceutical product for the prevention and/or treatment of autoimmune disease is provided based on the present invention. Therefore, the present invention can be utilized in the pharmaceutical manufacturing industry and the like.

The invention claimed is:

1. A method of suppressing complement alternative pathway in a mammalian subject in need thereof, comprising administering to the subject a therapeutically effective amount of C1 q and tumor necrosis factor related protein 6 (CTRP6) or a functional analog thereof, wherein the CTRP6 or functional analog comprises the amino acid sequence selected from the group consisting of:
   a) human CTRP6 (SEQ ID NO: 1); and
   b) the amino acid sequence having at least 95% sequence identity with C1 q domain of human CTRP6 and activity to suppress complement activation.

2. The method of claim 1, wherein the mammalian subject is a patient with an inflammatory disorder selected from the group consisting of rheumatoid arthritis, rheumatoid spondylitis, osteoarthritis, gout, type 1 diabetes, vitiligo, systemic lupus erythematosus, biliary cirrhosis, uveitis, vesicular pemphigoid, Graves' ophthalmopathy, multiple sclerosis, lupus, fibromyalgia, sepsis, septic shock, endotoxin shock, gram-negative bacterial sepsis, toxic shock syndrome, asthma, adult respiratory distress syndrome, chronic obstructive pulmonary disease, chronic pulmonary inflammation, Crohn's disease, psoriasis, eczema, ulcerative colitis, pancreatic fibrosis, hepatic fibrosis, acute and chronic nephropathy, irritable bowel syndrome, fever, restenosis, cerebral malaria, ischemic injury, nerve damage, Alzheimer's disease, Huntington's disease, Parkinson's disease, acute and chronic pain, allergic rhinitis, allergic conjunctivitis, chronic heart failure, acute coronary syndrome, and graft-versus-host reaction.

3. The method of claim 2, wherein the inflammatory disorder is selected from the group consisting of rheumatoid arthritis, rheumatoid spondylitis, type 1 diabetes, systemic lupus erythematosus, multiple sclerosis, lupus, and acute and chronic nephropathy.

4. The method of claim 2, wherein the inflammatory disorder is selected from the group consisting of rheumatoid arthritis, osteoarthritis, multiple sclerosis and psoriasis.

5. The method of claim 2, wherein the inflammatory disorder is selected from the group consisting of multiple sclerosis and psoriasis.

6. The method of claim 1, wherein the CTRP6 or functional analog is human CTRP6 (SEQ ID NO: 1).

7. A method of suppressing complement alternative pathway in a mammalian subject in need thereof, comprising administering to the subject a therapeutically effective amount of C1q and tumor necrosis factor related protein 6 (CTRP6) or a functional analog thereof, wherein the CTRP6 or functional analog comprises the amino acid sequence selected from the group consisting of: a) human CTRP6 (SEQ ID NO: 1); b) the amino acid sequence having at least 95% sequence identity with human CTRP6 and activity to suppress complement activation; and c) the amino acid sequence having at least 95% sequence identity with C1q domain of human CTRP6 and activity to suppress complement activation.

8. The method of claim 7, wherein the CTRP6 or functional analog comprises the amino acid sequence having at least 95% sequence identity with C1q domain of human CTRP6 and activity to suppress complement activation.

9. The method of claim 7, wherein the functional analog comprises human CTRP6 (SEQ ID NO: 1) with one or more substitutions selected from the group consisting of (a) valine for leucine, (b) arginine for lysine, and (c) asparagine for glutamine.

10. A method of suppressing complement alternative pathway in a mammalian subject in need thereof, comprising administering to the subject a therapeutically effective amount of a functional analog of C1q and tumor necrosis factor related protein 6 (CTRP6), wherein the functional analog comprises the amino acid sequence having at least 95% sequence identity with C1q domain of human CTRP6 and activity to suppress complement activation.

11. The method of claim 10, wherein the functional analog comprises human CTRP6 (SEQ ID NO: 1) having one or more substitutions in the C1q domain selected from the group consisting of (a) valine for leucine, (b) arginine for lysine, and (c) asparagine for glutamine.

12. The method of claim 10 for the treatment of an inflammatory disorder selected from the group consisting of rheumatoid arthritis, rheumatoid spondylitis, osteoarthritis, gout, type 1 diabetes, vitiligo, systemic lupus erythematosus, biliary cirrhosis, uveitis, vesicular pemphigoid, Graves' ophthalmopathy, multiple sclerosis, lupus, fibromyalgia, sepsis, septic shock, endotoxin shock, gram-negative bacterial sepsis, toxic shock syndrome, asthma, adult respiratory distress syndrome, chronic obstructive pulmonary disease, chronic pulmonary inflammation, Crohn's disease, psoriasis, eczema, ulcerative colitis, pancreatic fibrosis, hepatic fibrosis, acute and chronic nephropathy, irritable bowel syndrome, fever, restenosis, cerebral malaria, ischemic injury, nerve damage, Alzheimer's disease, Huntington's disease, Parkinson's disease, acute and chronic pain, allergic rhinitis, allergic conjunctivitis, chronic heart failure, acute coronary syndrome, and graft-versus-host reaction.

13. The method of claim 10 for the treatment of an inflammatory disorder selected from the group consisting of rheumatoid arthritis, rheumatoid spondylitis, type 1 diabetes, systemic lupus erythematosus, multiple sclerosis, lupus, and acute and chronic nephropathy.

* * * * *

SEQUENCE LISTING

```
<160> NUMBER OF SEQ ID NOS: 28

<210> SEQ ID NO 1
<211> LENGTH: 278
<212> TYPE: PRT
<213> ORGANISM: Homo sapiens

<400> SEQUENCE: 1

Met Gln Trp Leu Arg Val Arg Glu Ser Pro Gly Glu Ala Thr Gly His
1               5                   10                  15

Arg Val Thr Met Gly Thr Ala Ala Leu Gly Pro Val Trp Ala Ala Leu
            20                  25                  30

Leu Leu Phe Leu Leu Met Cys Glu Ile Pro Met Val Glu Leu Thr Phe
        35                  40                  45

Asp Arg Ala Val Ala Ser Gly Cys Gln Arg Cys Cys Asp Ser Glu Asp
    50                  55                  60
```

Pro Leu Asp Pro Ala His Val Ser Ser Ala Ser Ser Ser Gly Arg Pro
 65                  70                  75                  80

His Ala Leu Pro Glu Ile Arg Pro Tyr Ile Asn Ile Thr Ile Leu Lys
                 85                  90                  95

Gly Asp Lys Gly Asp Pro Gly Pro Met Gly Leu Pro Gly Tyr Met Gly
            100                 105                 110

Arg Glu Gly Pro Gln Gly Glu Pro Gly Pro Gln Gly Ser Lys Gly Asp
        115                 120                 125

Lys Gly Glu Met Gly Ser Pro Gly Ala Pro Cys Gln Lys Arg Phe Phe
130                 135                 140

Ala Phe Ser Val Gly Arg Lys Thr Ala Leu His Ser Gly Glu Asp Phe
145                 150                 155                 160

Gln Thr Leu Leu Phe Glu Arg Val Phe Val Asn Leu Asp Gly Cys Phe
                165                 170                 175

Asp Met Ala Thr Gly Gln Phe Ala Ala Pro Leu Arg Gly Ile Tyr Phe
            180                 185                 190

Phe Ser Leu Asn Val His Ser Trp Asn Tyr Lys Glu Thr Tyr Val His
        195                 200                 205

Ile Met His Asn Gln Lys Glu Ala Val Ile Leu Tyr Ala Gln Pro Ser
210                 215                 220

Glu Arg Ser Ile Met Gln Ser Gln Ser Val Met Leu Asp Leu Ala Tyr
225                 230                 235                 240

Gly Asp Arg Val Trp Val Arg Leu Phe Lys Arg Gln Arg Glu Asn Ala
                245                 250                 255

Ile Tyr Ser Asn Asp Phe Asp Thr Tyr Ile Thr Phe Ser Gly His Leu
            260                 265                 270

Ile Lys Ala Glu Asp Asp
        275

<210> SEQ ID NO 2
<211> LENGTH: 264
<212> TYPE: PRT
<213> ORGANISM: Mus musculus

<400> SEQUENCE: 2

Met Arg Val Ile Met Gly Ile Ala Ser Leu Gly Phe Leu Trp Ala Val
1               5                   10                  15

Phe Leu Leu Pro Leu Val Phe Gly Val Pro Thr Glu Glu Thr Thr Phe
                20                  25                  30

Gly Glu Ser Val Ala Ser His Leu Pro Lys Gly Cys Arg Arg Cys Cys
            35                  40                  45

Asp Pro Glu Asp Leu Met Ser Ser Asp Thr Val Gln Ala Pro Val
        50                  55                  60

Ser Pro Tyr Val Leu Pro Glu Val Arg Pro Tyr Ile Asn Ile Thr Ile
 65                  70                  75                  80

Leu Lys Gly Asp Lys Gly Asp Arg Gly Pro Thr Gly Thr Pro Gly Lys
                 85                  90                  95

Pro Gly Lys Asn Gly Thr Arg Gly Asp Arg Gly Ser Gln Gly Val Lys
            100                 105                 110

Gly Asp Lys Gly Gln Ala Gly Ser Pro Gly Ser Ser Cys Gln Thr His
        115                 120                 125

Tyr Ser Ala Phe Ser Val Gly Arg Lys Thr Gly Leu His Ser Ser Glu
    130                 135                 140

Asn Phe Leu Ser Leu Leu Phe Asp Arg Val Phe Val Asn Thr Asp Gly

```
                 145                 150                 155                 160
His Phe Asp Met Ala Thr Gly Ser Phe Val Ala Pro Leu Arg Gly Leu
                165                 170                 175

Tyr Phe Phe Ser Leu Asn Val His Ser Trp Asn Tyr Lys Glu Thr Tyr
                180                 185                 190

Val His Ile Val His Asn Glu Gln Ala Val Val Ile Leu Tyr Ala Gln
                195                 200                 205

Pro Ser Glu Arg Ser Ile Met Gln Ser Gln Ser Val Met Leu Pro Leu
                210                 215                 220

Val Pro Gly Asp Arg Val Trp Val Arg Leu Phe Lys Arg Glu Arg Glu
225                 230                 235                 240

Asn Gly Ile Tyr Ser Asp Asp Val Asp Thr Tyr Ile Thr Phe Ser Gly
                245                 250                 255

His Leu Ile Lys Ala Glu Asp Asn
                260

<210> SEQ ID NO 3
<211> LENGTH: 29
<212> TYPE: DNA
<213> ORGANISM: Artificial Sequence
<220> FEATURE:
<223> OTHER INFORMATION: Primer for C1qtnf6

<400> SEQUENCE: 3
tccccgcggc tccaaaccat gctgactct                                          29

<210> SEQ ID NO 4
<211> LENGTH: 28
<212> TYPE: DNA
<213> ORGANISM: Artificial Sequence
<220> FEATURE:
<223> OTHER INFORMATION: Primer for C1qtnf6

<400> SEQUENCE: 4
cgtctagaag cacctaactg catgctgg                                           28

<210> SEQ ID NO 5
<211> LENGTH: 30
<212> TYPE: DNA
<213> ORGANISM: Artificial Sequence
<220> FEATURE:
<223> OTHER INFORMATION: Primer for C1qtnf6

<400> SEQUENCE: 5
ccatcgatat ctgggcaagt ccccatgtct                                         30

<210> SEQ ID NO 6
<211> LENGTH: 30
<212> TYPE: DNA
<213> ORGANISM: Artificial Sequence
<220> FEATURE:
<223> OTHER INFORMATION: Primer for C1qtnf6

<400> SEQUENCE: 6
acgcgtcgac tcctcctggg tcattctgca                                         30

<210> SEQ ID NO 7
<211> LENGTH: 24
<212> TYPE: DNA
<213> ORGANISM: Artificial Sequence
<220> FEATURE:
<223> OTHER INFORMATION: Primer for C1qtnf6 deficient allele
```

```
<400> SEQUENCE: 7
ctctttctgg caagcacata gctc                                          24

<210> SEQ ID NO 8
<211> LENGTH: 24
<212> TYPE: DNA
<213> ORGANISM: Artificial Sequence
<220> FEATURE:
<223> OTHER INFORMATION: Primer for C1qtnf6 deficient allele

<400> SEQUENCE: 8
agaggaaccc aagcttctta cagg                                          24

<210> SEQ ID NO 9
<211> LENGTH: 22
<212> TYPE: DNA
<213> ORGANISM: Artificial Sequence
<220> FEATURE:
<223> OTHER INFORMATION: Primer for amplifying genome probe of C1qtnf6
      deficient allele

<400> SEQUENCE: 9
aacctgactt atgtgtgggc ag                                            22

<210> SEQ ID NO 10
<211> LENGTH: 22
<212> TYPE: DNA
<213> ORGANISM: Artificial Sequence
<220> FEATURE:
<223> OTHER INFORMATION: Primer for amplifying genome probe of C1qtnf6
      deficient allele

<400> SEQUENCE: 10
caggattgta tgagtgtctg gg                                            22

<210> SEQ ID NO 11
<211> LENGTH: 22
<212> TYPE: DNA
<213> ORGANISM: Artificial Sequence
<220> FEATURE:
<223> OTHER INFORMATION: Primer for amplifying genome probe of C1qtnf6
      deficient allele

<400> SEQUENCE: 11
agaggatgtg tgcgtagtcc aa                                            22

<210> SEQ ID NO 12
<211> LENGTH: 22
<212> TYPE: DNA
<213> ORGANISM: Artificial Sequence
<220> FEATURE:
<223> OTHER INFORMATION: Primer for amplifying genome probe of C1qtnf6
      deficient allele

<400> SEQUENCE: 12
tggatggaca gatggatgga tg                                            22

<210> SEQ ID NO 13
<211> LENGTH: 25
<212> TYPE: DNA
<213> ORGANISM: Artificial Sequence
<220> FEATURE:
<223> OTHER INFORMATION: Primer for detecting WT C1qtnf6 allele

<400> SEQUENCE: 13
ggcatctctg gtgcttacaa ccaag                                         25
```

<210> SEQ ID NO 14
<211> LENGTH: 26
<212> TYPE: DNA
<213> ORGANISM: Artificial Sequence
<220> FEATURE:
<223> OTHER INFORMATION: Primer for detecting nutated C1qtnf6 allele

<400> SEQUENCE: 14
agttatacgc gttcgctcgg taccca         26

<210> SEQ ID NO 15
<211> LENGTH: 26
<212> TYPE: DNA
<213> ORGANISM: Artificial Sequence
<220> FEATURE:
<223> OTHER INFORMATION: Primer for mouse C1qtnf6 genome

<400> SEQUENCE: 15
gacagcaagc tgatcatcca cactca         26

<210> SEQ ID NO 16
<211> LENGTH: 29
<212> TYPE: DNA
<213> ORGANISM: Artificial Sequence
<220> FEATURE:
<223> OTHER INFORMATION: RT-PCR primer for mouse C1qtnf6

<400> SEQUENCE: 16
ttgaattcgc aggatgaggg tcatcatgg      29

<210> SEQ ID NO 17
<211> LENGTH: 28
<212> TYPE: DNA
<213> ORGANISM: Artificial Sequence
<220> FEATURE:
<223> OTHER INFORMATION: RT-PCR primer for mouse C1qtnf6

<400> SEQUENCE: 17
cggaattcag ttgtcctctg ccttgatc       28

<210> SEQ ID NO 18
<211> LENGTH: 24
<212> TYPE: DNA
<213> ORGANISM: Artificial Sequence
<220> FEATURE:
<223> OTHER INFORMATION: Primer for C1qtnf6 Tg

<400> SEQUENCE: 18
acgtgctggt tgttgtgctg tctc           24

<210> SEQ ID NO 19
<211> LENGTH: 25
<212> TYPE: DNA
<213> ORGANISM: Artificial Sequence
<220> FEATURE:
<223> OTHER INFORMATION: Primer for C1qtnf6 Tg

<400> SEQUENCE: 19
ctttatagcc acctttgttc atggc          25

<210> SEQ ID NO 20
<211> LENGTH: 23
<212> TYPE: DNA
<213> ORGANISM: Artificial Sequence
<220> FEATURE:

```
<223> OTHER INFORMATION: Primer for C1qtnf6 Tg

<400> SEQUENCE: 20
ctacaggaac accagggaag cca                                              23

<210> SEQ ID NO 21
<211> LENGTH: 23
<212> TYPE: DNA
<213> ORGANISM: Artificial Sequence
<220> FEATURE:
<223> OTHER INFORMATION: Primer for C1qtnf6 Tg

<400> SEQUENCE: 21
ttgatcaggt ggccactgaa ggt                                              23

<210> SEQ ID NO 22
<211> LENGTH: 24
<212> TYPE: DNA
<213> ORGANISM: Artificial Sequence
<220> FEATURE:
<223> OTHER INFORMATION: Primer for C1qtnf6 Tg mouse

<400> SEQUENCE: 22
ctgtgtacgt tgaggctgaa gaag                                             24

<210> SEQ ID NO 23
<211> LENGTH: 24
<212> TYPE: DNA
<213> ORGANISM: Artificial Sequence
<220> FEATURE:
<223> OTHER INFORMATION: Primer for C1qtnf6 Tg mouse

<400> SEQUENCE: 23
tggcctcagt ttcacttctg caga                                             24

<210> SEQ ID NO 24
<211> LENGTH: 24
<212> TYPE: DNA
<213> ORGANISM: Artificial Sequence
<220> FEATURE:
<223> OTHER INFORMATION: Primer for C1qtnf6 Tg mouse

<400> SEQUENCE: 24
atcctaaagg gtgacaaagg ggac                                             24

<210> SEQ ID NO 25
<211> LENGTH: 837
<212> TYPE: DNA
<213> ORGANISM: Homo sapiens
<220> FEATURE:
<221> NAME/KEY: CDS
<222> LOCATION: (1)..(834)

<400> SEQUENCE: 25 atg cag tgg ctc agg gtc cgt gag tcg cct ggg gag gcc aca gga cac        48
Met Gln Trp Leu Arg Val Arg Glu Ser Pro Gly Glu Ala Thr Gly His
  1               5                  10                  15 agg gtc acc atg ggg aca gcc gcc ctg ggt ccc gtc tgg gca gcg ctc        96
Arg Val Thr Met Gly Thr Ala Ala Leu Gly Pro Val Trp Ala Ala Leu
             20                  25                  30 ctg ctc ttt ctc ctg atg tgt gag atc cct atg gtg gag ctc acc ttt       144
Leu Leu Phe Leu Leu Met Cys Glu Ile Pro Met Val Glu Leu Thr Phe
         35                  40                  45 gac aga gct gtg gcc agc ggc tgc caa cgg tgc tgt gac tct gag gac       192
Asp Arg Ala Val Ala Ser Gly Cys Gln Arg Cys Cys Asp Ser Glu Asp
```

```
                50                  55                  60
ccc ctg gat cct gcc cat gta tcc tca gcc tct tcc tcc ggc cgc ccc      240
Pro Leu Asp Pro Ala His Val Ser Ser Ala Ser Ser Ser Gly Arg Pro
 65                  70                  75                  80 cac gcc ctg cct gag atc aga ccc tac att aat atc acc atc ctg aag      288
His Ala Leu Pro Glu Ile Arg Pro Tyr Ile Asn Ile Thr Ile Leu Lys
                 85                  90                  95 ggt gac aaa ggg gac cca ggc cca atg ggc ctg cca ggg tac atg ggc      336
Gly Asp Lys Gly Asp Pro Gly Pro Met Gly Leu Pro Gly Tyr Met Gly
            100                 105                 110 agg gag ggt ccc caa ggg gag cct ggc cct cag ggc agc aag ggt gac      384
Arg Glu Gly Pro Gln Gly Glu Pro Gly Pro Gln Gly Ser Lys Gly Asp
        115                 120                 125 aag ggg gag atg ggc agc ccc ggc gcc ccg tgc cag aag cgc ttc ttc      432
Lys Gly Glu Met Gly Ser Pro Gly Ala Pro Cys Gln Lys Arg Phe Phe
    130                 135                 140 gcc ttc tca gtg ggc cgc aag acg gcc ctg cac agc ggc gag gac ttc      480
Ala Phe Ser Val Gly Arg Lys Thr Ala Leu His Ser Gly Glu Asp Phe
145                 150                 155                 160 cag acg ctg ctc ttc gaa agg gtc ttt gtg aac ctt gat ggg tgc ttt      528
Gln Thr Leu Leu Phe Glu Arg Val Phe Val Asn Leu Asp Gly Cys Phe
                165                 170                 175 gac atg gcg acc ggc cag ttt gct gct ccc ctg cgt ggc atc tac ttc      576
Asp Met Ala Thr Gly Gln Phe Ala Ala Pro Leu Arg Gly Ile Tyr Phe
            180                 185                 190 ttc agc ctc aat gtg cac agc tgg aat tac aag gag acg tac gtg cac      624
Phe Ser Leu Asn Val His Ser Trp Asn Tyr Lys Glu Thr Tyr Val His
        195                 200                 205 att atg cat aac cag aaa gag gct gtc atc ctg tac gcg cag ccc agc      672
Ile Met His Asn Gln Lys Glu Ala Val Ile Leu Tyr Ala Gln Pro Ser
    210                 215                 220 gag cgc agc atc atg cag agc cag agt gtg atg ctg gac ctg gcc tac      720
Glu Arg Ser Ile Met Gln Ser Gln Ser Val Met Leu Asp Leu Ala Tyr
225                 230                 235                 240 ggg gac cgc gtc tgg gtg cgg ctc ttc aag cgc cag cgc gag aac gcc      768
Gly Asp Arg Val Trp Val Arg Leu Phe Lys Arg Gln Arg Glu Asn Ala
                245                 250                 255 atc tac agc aac gac ttc gac acc tac atc acc ttc agc ggc cac ctc      816
Ile Tyr Ser Asn Asp Phe Asp Thr Tyr Ile Thr Phe Ser Gly His Leu
            260                 265                 270 atc aag gcc gag gac gac tga                                          837
Ile Lys Ala Glu Asp Asp
        275

<210> SEQ ID NO 26
<211> LENGTH: 278
<212> TYPE: PRT
<213> ORGANISM: Homo sapiens

<400> SEQUENCE: 26

Met Gln Trp Leu Arg Val Arg Glu Ser Pro Gly Glu Ala Thr Gly His
 1               5                  10                  15

Arg Val Thr Met Gly Thr Ala Ala Leu Gly Pro Val Trp Ala Ala Leu
            20                  25                  30

Leu Leu Phe Leu Leu Met Cys Glu Ile Pro Met Val Glu Leu Thr Phe
        35                  40                  45

Asp Arg Ala Val Ala Ser Gly Cys Gln Arg Cys Cys Asp Ser Glu Asp
    50                  55                  60

Pro Leu Asp Pro Ala His Val Ser Ser Ala Ser Ser Ser Gly Arg Pro
```

```
                65                  70                  75                  80
His Ala Leu Pro Glu Ile Arg Pro Tyr Ile Asn Ile Thr Ile Leu Lys
                    85                  90                  95

Gly Asp Lys Gly Asp Pro Gly Pro Met Gly Leu Pro Gly Tyr Met Gly
                100                 105                 110

Arg Glu Gly Pro Gln Gly Glu Gly Pro Gln Gly Ser Lys Gly Asp
            115                 120                 125

Lys Gly Glu Met Gly Ser Pro Gly Ala Pro Cys Gln Lys Arg Phe Phe
        130                 135                 140

Ala Phe Ser Val Gly Arg Lys Thr Ala Leu His Ser Gly Glu Asp Phe
145                 150                 155                 160

Gln Thr Leu Leu Phe Glu Arg Val Phe Val Asn Leu Asp Gly Cys Phe
                165                 170                 175

Asp Met Ala Thr Gly Gln Phe Ala Ala Pro Leu Arg Gly Ile Tyr Phe
                180                 185                 190

Phe Ser Leu Asn Val His Ser Trp Asn Tyr Lys Glu Thr Tyr Val His
                195                 200                 205

Ile Met His Asn Gln Lys Glu Ala Val Ile Leu Tyr Ala Gln Pro Ser
        210                 215                 220

Glu Arg Ser Ile Met Gln Ser Gln Ser Val Met Leu Asp Leu Ala Tyr
225                 230                 235                 240

Gly Asp Arg Val Trp Val Arg Leu Phe Lys Arg Gln Arg Glu Asn Ala
                245                 250                 255

Ile Tyr Ser Asn Asp Phe Asp Thr Tyr Ile Thr Phe Ser Gly His Leu
                260                 265                 270

Ile Lys Ala Glu Asp Asp
        275

<210> SEQ ID NO 27
<211> LENGTH: 795
<212> TYPE: DNA
<213> ORGANISM: Mus musculus
<220> FEATURE:
<221> NAME/KEY: CDS
<222> LOCATION: (1)..(792)

<400> SEQUENCE: 27 atg agg gtc atc atg ggg ata gcc agc ctg ggg ttc ctc tgg gca gta     48
Met Arg Val Ile Met Gly Ile Ala Ser Leu Gly Phe Leu Trp Ala Val
1               5                   10                  15 ttc ctg ctt cct ctt gtg ttt ggg gtc ccc aca gag gag act acc ttt     96
Phe Leu Leu Pro Leu Val Phe Gly Val Pro Thr Glu Glu Thr Thr Phe
            20                  25                  30 gga gaa tct gtg gcc tcc cat ctc ccc aaa ggc tgt cga cga tgc tgt    144
Gly Glu Ser Val Ala Ser His Leu Pro Lys Gly Cys Arg Arg Cys Cys
        35                  40                  45 gac ccc gag gac ctg atg tcc tct gat gat acg gtc cag gcc cct gtt    192
Asp Pro Glu Asp Leu Met Ser Ser Asp Asp Thr Val Gln Ala Pro Val
    50                  55                  60 tcc cct tat gtc ctg cct gaa gtc agg ccg tac atc aac att act atc    240
Ser Pro Tyr Val Leu Pro Glu Val Arg Pro Tyr Ile Asn Ile Thr Ile
65                  70                  75                  80 cta aag ggt gac aaa ggg gac aga ggt cct aca gga aca cca ggg aag    288
Leu Lys Gly Asp Lys Gly Asp Arg Gly Pro Thr Gly Thr Pro Gly Lys
                85                  90                  95 cca ggc aag aat ggt acc cga ggg gac cgt ggc tct cag ggt gtc aaa    336
Pro Gly Lys Asn Gly Thr Arg Gly Asp Arg Gly Ser Gln Gly Val Lys
            100                 105                 110
```

-continued

```
ggt gac aag ggg cag gca ggt agc cct ggc agc tcg tgc cag aca cat       384
Gly Asp Lys Gly Gln Ala Gly Ser Pro Gly Ser Ser Cys Gln Thr His
            115                 120                 125 tac tca gcc ttc tct gtg ggc cgc aag act ggc ttg cac agc agc gag       432
Tyr Ser Ala Phe Ser Val Gly Arg Lys Thr Gly Leu His Ser Ser Glu
        130                 135                 140 aac ttc ctc tca ctg ctg ttc gac agg gtc ttt gtg aac acg gat ggc       480
Asn Phe Leu Ser Leu Leu Phe Asp Arg Val Phe Val Asn Thr Asp Gly
145                 150                 155                 160 cac ttt gac atg gcc act ggc agc ttt gtg gct ccc ctg cgc ggc ctc       528
His Phe Asp Met Ala Thr Gly Ser Phe Val Ala Pro Leu Arg Gly Leu
                165                 170                 175 tac ttc ttc agc ctc aac gta cac agc tgg aac tac aag gag acc tac       576
Tyr Phe Phe Ser Leu Asn Val His Ser Trp Asn Tyr Lys Glu Thr Tyr
            180                 185                 190 gtg cac atc gtg cac aat gag cag gca gtg gtg atc ctg tac gcg cag       624
Val His Ile Val His Asn Glu Gln Ala Val Val Ile Leu Tyr Ala Gln
        195                 200                 205 ccc agc gaa cgc agc atc atg cag agc cag agt gtg atg ctg cca ctg       672
Pro Ser Glu Arg Ser Ile Met Gln Ser Gln Ser Val Met Leu Pro Leu
210                 215                 220 gtg ccg ggt gac cgt gtg tgg gtg cgg ctc ttc aag cgg gag cgg gaa       720
Val Pro Gly Asp Arg Val Trp Val Arg Leu Phe Lys Arg Glu Arg Glu
225                 230                 235                 240 aac ggc atc tac agt gat gac gtg gac acg tac atc acc ttc agt ggc       768
Asn Gly Ile Tyr Ser Asp Asp Val Asp Thr Tyr Ile Thr Phe Ser Gly
                245                 250                 255 cac ctg atc aag gca gag gac aac tga                                   795
His Leu Ile Lys Ala Glu Asp Asn
            260
```

<210> SEQ ID NO 28
<211> LENGTH: 264
<212> TYPE: PRT
<213> ORGANISM: Mus musculus

<400> SEQUENCE: 28

```
Met Arg Val Ile Met Gly Ile Ala Ser Leu Gly Phe Leu Trp Ala Val
1               5                   10                  15

Phe Leu Leu Pro Leu Val Phe Gly Val Pro Thr Glu Glu Thr Thr Phe
            20                  25                  30

Gly Glu Ser Val Ala Ser His Leu Pro Lys Gly Cys Arg Arg Cys Cys
        35                  40                  45

Asp Pro Glu Asp Leu Met Ser Ser Asp Thr Val Gln Ala Pro Val
    50                  55                  60

Ser Pro Tyr Val Leu Pro Glu Val Arg Pro Tyr Ile Asn Ile Thr Ile
65                  70                  75                  80

Leu Lys Gly Asp Lys Gly Asp Arg Gly Pro Thr Gly Thr Pro Gly Lys
                85                  90                  95

Pro Gly Lys Asn Gly Thr Arg Gly Asp Arg Gly Ser Gln Gly Val Lys
            100                 105                 110

Gly Asp Lys Gly Gln Ala Gly Ser Pro Gly Ser Ser Cys Gln Thr His
        115                 120                 125

Tyr Ser Ala Phe Ser Val Gly Arg Lys Thr Gly Leu His Ser Ser Glu
    130                 135                 140

Asn Phe Leu Ser Leu Leu Phe Asp Arg Val Phe Val Asn Thr Asp Gly
145                 150                 155                 160
```

```
His Phe Asp Met Ala Thr Gly Ser Phe Val Ala Pro Leu Arg Gly Leu
                165                 170                 175

Tyr Phe Phe Ser Leu Asn Val His Ser Trp Asn Tyr Lys Glu Thr Tyr
            180                 185                 190

Val His Ile Val His Asn Glu Gln Ala Val Val Ile Leu Tyr Ala Gln
        195                 200                 205

Pro Ser Glu Arg Ser Ile Met Gln Ser Gln Ser Val Met Leu Pro Leu
        210                 215                 220

Val Pro Gly Asp Arg Val Trp Val Arg Leu Phe Lys Arg Glu Arg Glu
225                 230                 235                 240

Asn Gly Ile Tyr Ser Asp Asp Val Asp Thr Tyr Ile Thr Phe Ser Gly
            245                 250                 255

His Leu Ile Lys Ala Glu Asp Asn
            260
```